(12) United States Patent
Hete et al.

(10) Patent No.: US 11,491,293 B2
(45) Date of Patent: Nov. 8, 2022

(54) METHOD AND SYSTEM FOR DELIVERING OXYGEN TO A PATIENT

(71) Applicant: KONINKLIJKE PHILIPS N.V., Eindhoven (NL)

(72) Inventors: Bernard F Hete, Kittanning, PA (US); Charles Edward Murray, Jeannette, PA (US)

(73) Assignee: Koninklijke Philips N.V., Eindhoven (NL)

(*) Notice: Subject to any disclaimer, the term of this patent is extended or adjusted under 35 U.S.C. 154(b) by 446 days.

(21) Appl. No.: 16/718,837

(22) Filed: Dec. 18, 2019

(65) Prior Publication Data

US 2020/0398013 A1 Dec. 24, 2020

Related U.S. Application Data

(60) Provisional application No. 62/786,572, filed on Dec. 31, 2018.

(51) Int. Cl.
| | |
|---|---|
| A61M 16/00 | (2006.01) |
| A61M 16/06 | (2006.01) |
| A61M 16/10 | (2006.01) |
| A61M 16/20 | (2006.01) |

(52) U.S. Cl.
CPC .... A61M 16/0672 (2014.02); A61M 16/0003 (2014.02); A61M 16/101 (2014.02); A61M 16/201 (2014.02)

(58) Field of Classification Search
CPC .............. A61M 16/101; A61M 16/201; A61M 16/0677; A61M 16/202; A61M 16/024; A61M 16/125
See application file for complete search history.

(56) References Cited

U.S. PATENT DOCUMENTS

| | | |
|---|---|---|
| 2005/0274381 A1 | 12/2005 | Deane et al. |
| 2007/0044799 A1 | 3/2007 | Hete et al. |
| 2008/0295837 A1 | 12/2008 | McCormick et al. |
| 2010/0116270 A1 | 5/2010 | Armstrong et al. |

(Continued)

OTHER PUBLICATIONS

International Search Report for PCT/EP2019/085213 dated Dec. 16, 2019.

(Continued)

*Primary Examiner* — Margaret M Luarca

(74) *Attorney, Agent, or Firm* — Daniel H. Brean; Andrew M. Gabriel

(57) ABSTRACT

A system for delivering oxygen comprises an oxygen source; a ventilator operatively connected to the oxygen source to receive a supply of oxygen therefrom; a valve having a) an open position in which the ventilator receives the supply of oxygen from the oxygen source and b) a closed position in which the ventilator is not in fluid communication with the oxygen source; a sensor configured to measure breath flow information for the patient; and a computer system to: determine a volume of gas delivered to the patient during a breath cycle of the patient and an inspiratory volume of gas delivered to the patient during an inspiration phase of the breath cycle by using the breath flow information; and provide input to the valve based on the determined volumes, the provided input causing a movement of the valve between the open and the closed positions.

18 Claims, 23 Drawing Sheets

(56) References Cited

U.S. PATENT DOCUMENTS

| | | | |
|---|---|---|---|
| 2012/0006326 A1 | 1/2012 | Ahmad | |
| 2016/0279363 A1* | 9/2016 | DeVries | A61M 16/201 |
| 2017/0113013 A1 | 4/2017 | Allum | |
| 2018/0154102 A1* | 6/2018 | Selander | A61M 16/024 |

OTHER PUBLICATIONS

Gangidine, M. M. et al., "System Design Verification for Closed Loop Control of Oxygenation with Concentrator Integration". Military Medicine, 181, 5:1777, 2016.

Rodriquez, D., Jr. et al., "Maximizing Oxygen Delivery During Mechanical Ventilation with a Portable Oxygen Concentrator". The Journal of Trauma, Injury, Infection, and Critical Care, vol. 69, No. 1, July Supplement 2010.

* cited by examiner

| Pressure (cmH2O) | Flow (L/min) | Volume @ 2 sec (L) | Pressure (cmH2O) | Flow (L/min) | Volume @ 2 sec (L) |
|---|---|---|---|---|---|
| 5 | 18.3 | 0.61 | 40 | 62.6 | 2.09 |
| 10 | 28.0 | 0.93 | 45 | 66.8 | 2.23 |
| 15 | 35.7 | 1.19 | 50 | 70.9 | 2.39 |
| 20 | 42.2 | 1.41 | 55 | 74.7 | 2.49 |
| 25 | 48.0 | 1.60 | 60 | 78.3 | 2.61 |
| 30 | 53.2 | 1.77 | 65 | 81.8 | 2.73 |
| 35 | 58.1 | 1.94 | 70 | 85.2 | 2.84 |

FIG. 12

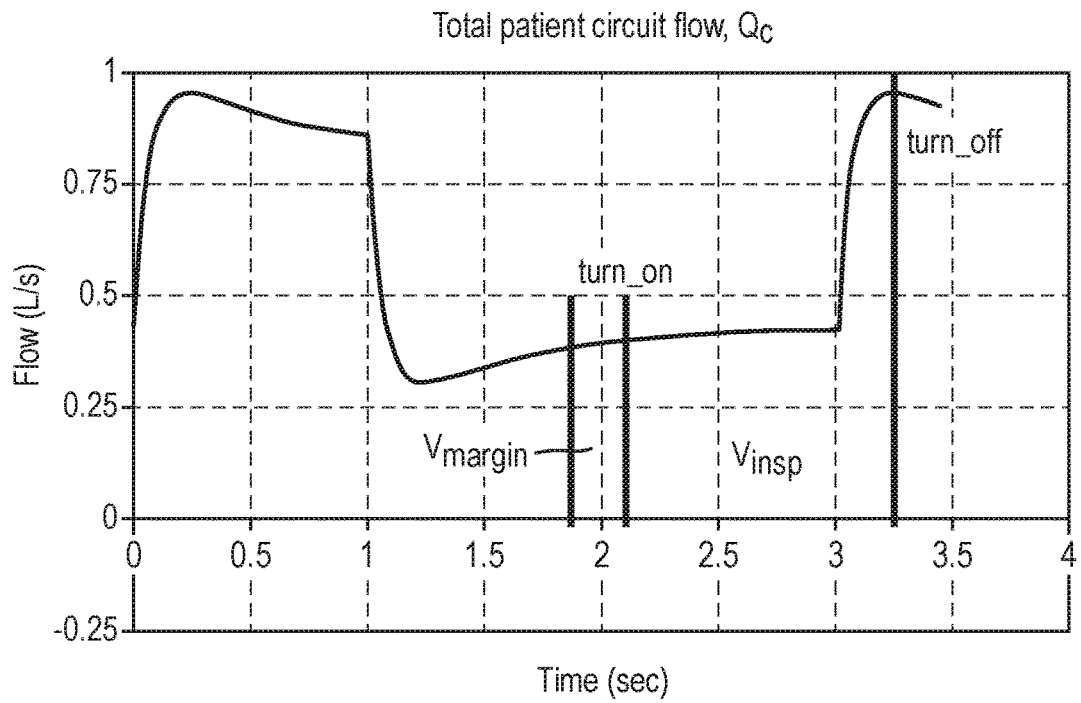
FIG. 22
| $V_{tube}$ | Elevation | Atmospheric pressure | Compliance | $\Delta P$ | Compliance value | % $V_{tube}$ |
|---|---|---|---|---|---|---|
| (cc) | (ft) | (cmH$_2$O) | (cc/cmH$_2$O) | (cmH$_2$O) | (cc) | (%) |
| 700 | 900 | 1000 | 0.70 | 20 | 14.0 | 2.0 |
| 1320 | 900 | 1000 | 1.32 | 20 | 26.4 | 2.0 |
| 1320 | 10,000 | 700 | 1.89 | 20 | 37.7 | 2.9 |
| 1320 | 10,000 | 700 | 1.89 | 40 | 75.4 | 5.7 |
FIG. 23
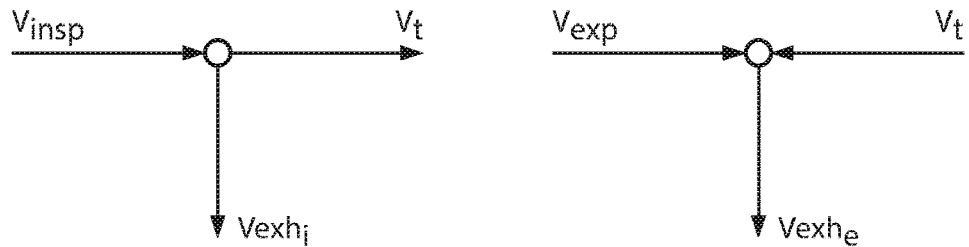
FIG. 24

| Parameter | Units | Parameter range | Lower % saved | Upper % saved | Δ % saved | Curve slope |
|---|---|---|---|---|---|---|
| CPAP | $cmH_2O$ | 2 - 25 | 28 | 58 | 30 | + |
| IPAP | $cmH_2O$ | 5 - 25 | 30 | 44 | 14 | - |
| EPAP | $cmH_2O$ | 5 - 25 | 30 | 58 | 28 | + |
| Tidal volume | mL | 200 - 950 | 38 | 61 | 23 | - |
| Breath rate | brpm | 5 - 20 | 37 | 59 | 22 | - |
| I:E | - | 1:1 - 1:5 | 35 | 68 | 33 | + |
| Additional leak | L/min | 0 - 25 | 52 | 58 | 6 | + |

FIG. 33

METHOD AND SYSTEM FOR DELIVERING OXYGEN TO A PATIENT

CROSS-REFERENCE TO RELATED APPLICATIONS

This patent application claims the priority benefit under 35 U.S.C. § 119(e) of U.S. Provisional Application No. 62/786,572, filed on Dec. 31, 2018, the contents of which are herein incorporated by reference.

BACKGROUND

1. Field

The present disclosure pertains to a method and a system for delivery oxygen to a patient.

2. Description of the Related Art

When mechanically ventilating patients, the patient is typically attached to a ventilator with a light-weight plastic breathing tube or circuit. With the advent of pressure support ventilation, the simplest and most commonly used patient circuit employs a passive exhalation valve near the patient, which is essentially just a hole in the patient circuit. This hole continuously exhausts gas from the patient circuit, which allows exhaled $CO_2$ to be removed from the patient circuit to avoid rebreathing. Because of this leak, there is a reasonably large bias flow from the ventilator continuously during use. This leak is fine for normal ventilation, but if an additional gas is added into the bulk flow from the ventilator, much of that presumably important gas is both wasted or diluted or both, because it never reaches the airways of the patient. Two gases of particular interest are supplemental oxygen and water vapor (humidification).

When an oxygen concentrator is used to deliver a constant flow of oxygen into a low-flow port of the pressure support ventilator, the effective $FiO_2$ delivered to the patient is lowered by the fact that some usually large fraction of the gas is dumped to atmosphere via the exhalation valve. That is, when using the oxygen concentrator with a non-invasive (NIV) mechanical ventilator, gas is delivered into the low-flow port on the ventilator. The oxygen concentrator is set to a constant flowrate so that its delivered oxygen mixes with the air from the NIV ventilator. Most NIV ventilator circuits are of the passive type, meaning that there is a constant leak from the exhalation valve, resulting in that only a fraction of the oxygen delivered by the ventilator actually is inhaled by the patient. Most of the gas exits the exhalation valve.

Waste of the oxygen concentrator is not a problem since the oxygen is just coming from the air in the room anyway. However, a flow rate of, for example, 5 Liters/minute (L/min) is pretty low compared with a typical flow of gas down the passive flow circuit, resulting in a limited $FiO_2$ that can be delivered. Increasing the $FiO_2$ on the other hand, would be valuable.

The pressure support mechanical ventilators may also have an accessory oxygen blending module (OBM) that possesses an oxygen Diameter Index Safety System (DISS) fitting to receive wall or bottled gas at a mean 50 pounds per square inch (psi) supply pressure. The oxygen blending module is then used by the ventilator to maintain a fractional oxygen of all gas that exits the ventilator to a value dialed in by the user. The only potential problem with this arrangement is that there is much waste of the oxygen, particularly when using a passive patient circuit that employs a fixed orifice that leaks gas directly to the atmosphere. In such a configuration, oxygen continuously bleeds from the exhalation valve even during the exhalation phase of breathing. During normal operation in a hospital or other facility, where the patient is not mobile, wall gas is available. Oxygen to the Oxygen Blending Module will be supplied from the wall source. In general, because of the plentiful supply of the wall oxygen, there is little concern for oxygen wastage. That is, when using the wall gas, the oxygen waste is not so much of a problem. But, when a patient is being transported within or outside of the hospital and bottled gas is used, the result is fast depletion of the gas bottle. That is, in cases where a patient needs controlled supplemental oxygen at a specific $FiO_2$ while they are being transported and unable to connect to the wall oxygen, the ventilator will be connected to a bottled gas. In such cases, wastage of bottled gas, which is expensive, heavy and occupies a large volume, is highly undesirable and is frankly a source of complaint for many users of such systems.

Also, when a bottled oxygen is used to deliver a constant flow of oxygen into a low-flow port of a pressure support ventilator, there is much waste of the oxygen, particularly when using a passive patient circuit that employs a fixed orifice that leaks exhalation gas directly to the atmosphere. In such a configuration, oxygen continuously bleeds from the exhalation valve even during the exhalation phase of breathing. The result is fast depletion of the gas bottle.

SUMMARY

Accordingly, it is an object of one or more embodiments of the present patent application to provide a system for delivering oxygen. The system comprises an oxygen source; a ventilator operatively connected to the oxygen source to receive a supply of oxygen therefrom, the ventilator configured to provide gas including a mixture of the supply of oxygen and air to a patient through a breathing circuit; a valve operatively connected to the ventilator and the oxygen source, the valve having a) an open position in which the ventilator receives the supply of oxygen from the oxygen source and b) a closed position in which the ventilator is not in fluid communication with the oxygen source; and a computer system that comprises one or more physical processors operatively connected with the sensor and the valve, the one or more physical processors being programmed with computer program instructions which, when executed cause the computer system to: determine a volume of gas delivered to the patient during a breath cycle of the patient and an inspiratory volume of gas delivered to the patient during an inspiration phase of the breath cycle by using the breath flow information; and provide input to the valve based on the determined volumes, the provided input causing a movement of the valve between the open and the closed positions.

It is yet another aspect of one or more embodiments of the present patent application to provide a method for delivering oxygen. The method is implemented by a computer system comprising one or more physical processors executing computer program instructions that, when executed, perform the method. The method comprises obtaining, from a sensor, breath flow information for a patient; determining, using the computer system, a volume of gas delivered to the patient during a breath cycle of the patient and an inspiratory volume of gas delivered to the patient during an inspiration phase of the breath cycle by using the breath flow information; and providing, using the computer system. input to a valve based on the determined volumes, the provided input causing a movement of the valve between an open position in which a ventilator receives a supply of oxygen from an oxygen source and a closed position in which the ventilator is not in fluid communication with the oxygen source.

It is yet another aspect of one or more embodiments to provide a system for delivering oxygen. The system comprises a means for supplying oxygen; a means for providing gas to a patient through a breathing circuit means, the gas including a mixture of air and a supply of oxygen from the means for supplying oxygen; an opening and closing means having a) an open position in which the means for providing gas receives the supply of oxygen from the means for supplying oxygen and b) a closed position in which the means for providing gas is not in fluid communication with the means for supplying oxygen; and a means for executing machine-readable instructions with at least one processor. The machine-readable instructions comprise obtaining, from a means for sensing, breath flow information for the patient; determining, using the means for executing, a volume of gas delivered to the patient during a breath cycle of the patient and an inspiratory volume of gas delivered to the patient during an inspiration phase of the breath cycle by using the breath flow information; and providing, using the means for executing, input to a valve based on the determined volumes, the provided input causing a movement of the opening and closing means between the open and closed positions.

These and other objects, features, and characteristics of the present patent application, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present patent application.

BRIEF DESCRIPTION OF THE DRAWINGS

FIG. 12 is a table showing flows versus circuit pressure in accordance with an embodiment of the present patent application;

FIG. 22 shows an exemplary graphical representation of total patient circuit flow with a margin added to the turn_on in accordance with an embodiment of the present patent application;

FIG. 23 is a table showing samples of tubing gas compression compliance results in accordance with an embodiment of the present patent application;

FIG. 24 shows gas volume movement during the inspiratory phase in the left figure, while gas volume movement during the expiratory phase in the right figure in accordance with an embodiment of the present patent application;

FIG. 33 is a table showing summary of % saved ranges for each of the parameters used in the model in accordance with an embodiment of the present patent application.

DETAILED DESCRIPTION OF EXEMPLARY EMBODIMENTS

Figure 1:
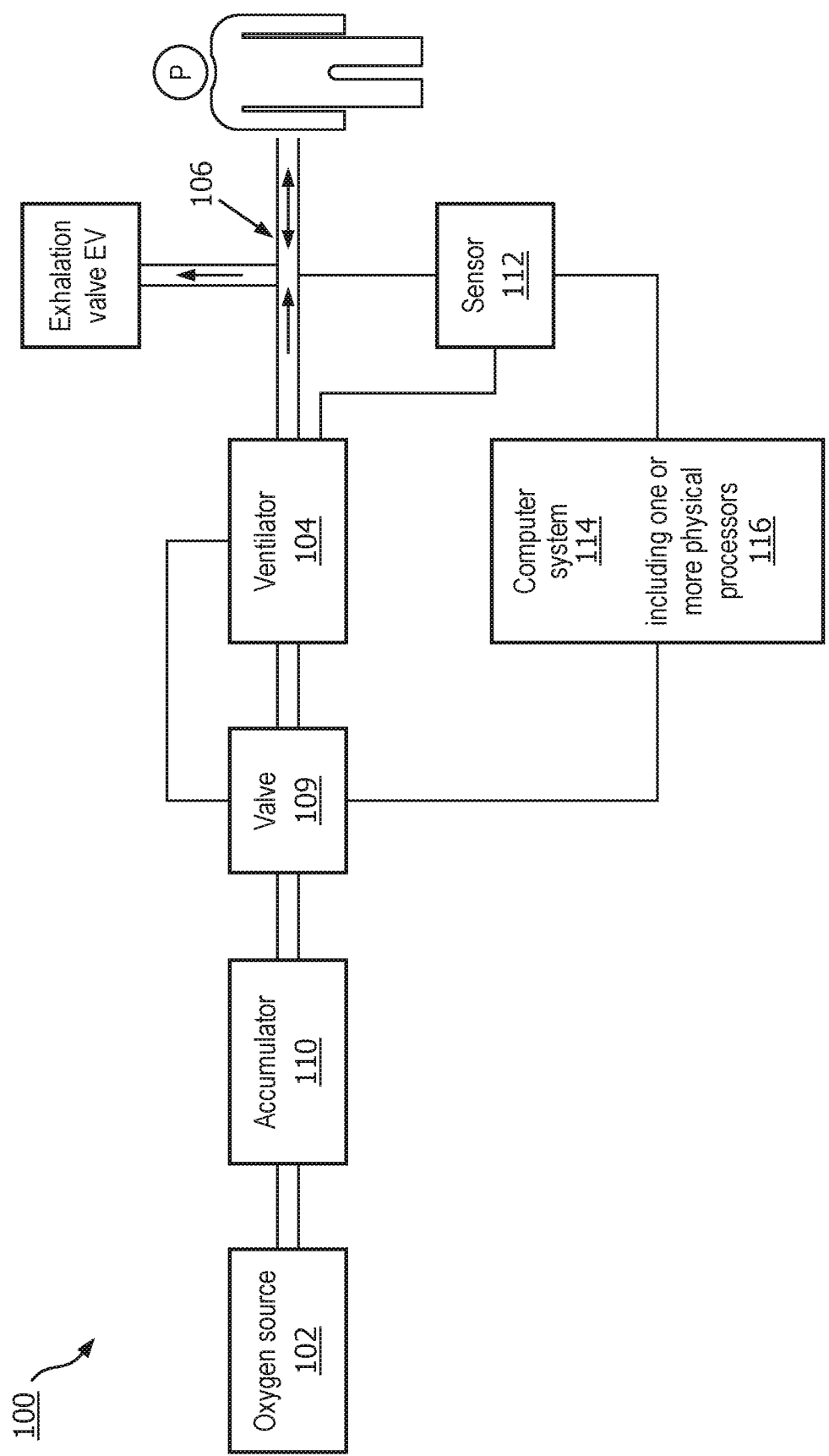
FIG. 1 shows a system for delivering oxygen to a patient in accordance with an embodiment of the present patent application.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, the term "or" means "and/or" unless the context clearly dictates otherwise.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present patent application provides a system 100 for delivering oxygen. System 100 comprises an oxygen source 102, a ventilator 104, a valve 108, a sensor 112 and a computer system 114. Ventilator 104 is operatively connected to oxygen source 102 to receive a supply of oxygen therefrom. Ventilator 104 is configured to provide gas including a mixture of the supply of oxygen and air to a patient through a breathing circuit 106. Ventilator 104 is configured to mix the supply of oxygen with ambient air drawn by ventilator 104 and provide the mixed oxygen and air to a patient through a breathing circuit 106. Valve 108 is operatively connected to ventilator 104 and oxygen source 102. Valve 108 has a) an open position in which the ventilator 104 receives the supply of oxygen from oxygen source 102 and b) a closed position in which the ventilator 104 is not in fluid communication with oxygen source 102. Sensor 112 is configured to measure breath flow information for the patient. Computer system 114 comprises one or more physical processors 116 operatively connected with the sensor 112 and valve 108. One or more physical processors 116 are programmed with computer program instructions which, when executed cause the computer system 114 to: determine a volume of gas delivered to the patient during a breath cycle of the patient, $V_{tot}$ and an inspiratory volume of gas delivered to the patient during an inspiration phase of the breath cycle, $V_{insp}$ by using the breath flow information; and provide input to the valve based on the determined volumes, the provided input causing a movement of valve 108 between the open and the closed positions.

In some embodiments, when oxygen source 102 is an oxygen concentrator, system 100 includes an accumulator 110 that is configured to accumulate the supply of oxygen from oxygen source 102 when valve 108 is in the closed position and to provide the supply of oxygen to ventilator 104 when valve 108 is in the open position. In some embodiments, as will be described in detail in the discussions below, accumulator 110 is functionally only needed to enhance $FiO_2$ when using oxygen concentrator 102 (as the oxygen source) through a low-flow port 124 of ventilator 104. In some embodiments, as will be described in detail in the discussions below, when using the low-flow gas bottle gas and the oxygen blending module as the oxygen source through low-flow port 124 of ventilator 104, the low-flow gas bottle gas and the oxygen blending module are configured to operate and garner the oxygen savings benefits of the method of the present patent application without a specific accumulator.

In some embodiments, computer system 114 is further configured to: obtain a tube volume, $V_{tube}$; and determine a volume difference between the volume of the gas delivered to the patient during the breath cycle of the patient, $V_{tot}$ and the tube volume, $V_{tube}$. In some embodiments, computer system 114 is configured to provide input to the valve causing the movement of valve 108 to the open position when the determined volume difference is delivered to the patient from a start of a next breath cycle. In some embodiments, computer system 114 is configured to maintain valve 108 in the open position until the inspiratory volume of gas delivered to the patient during the inspiration phase of the breath cycle and provide input to valve 108 causing the movement of valve 108 to the closed position after the inspiratory volume of gas is delivered to the patient.

In some embodiments, system 100 provides a flow of gas, such as oxygen, to a non-invasive ventilator (i.e., a ventilator with a passive exhalation port) at a location that is not on the patient circuit and that uses valve 108 to control the delivery of the gas to ventilator 104.

In some embodiments, system 100 is configured to increase or improve a desired fraction of inspired oxygen ($FiO_2$) from oxygen concentrator 102 to ventilator 104. In some embodiments, system 100 is configured to enhance $Fio_2$ from oxygen concentrator 102 to ventilator 104. In some embodiments, system 100 is configured to improve the limited $FiO_2$ associated with use of oxygen concentrator 102 input to low-flow port 124 (e.g., see FIGS. 2 and 3) of pressure support ventilator 104.

The present patent application provides valve 108 operating in concert with the breathing phase of patient P via ventilator 104. Valve 108 is used to shut off the oxygen flow to ventilator 104 and accumulate this oxygen gas in accumulator 110 to be delivered during the next time valve 108 is opened to deliver the oxygen gas into ventilator 104. The present patent application also provides an algorithm (as described in great detail below) that is used in ventilator 104 to drive valve 108 to allow delivery of the oxygen gas so that the oxygen gas only enters the ventilator 104 if the oxygen gas is going to be delivered to patient P during the inspiratory phase of patient P. In some embodiments, the algorithm is provided in ventilator 104. In some embodiments, the algorithm is provided in a stand-alone system other than ventilator 104.

In some embodiments, accumulator or high-pressure hose 110 takes advantage of the fact that oxygen concentrator 102 ultimately delivers gas at a pressure of about 8 psi. This pressure never reaches low-flow port 124 of ventilator 104 because the flow is unobstructed to and through ventilator 104. With valve 108 though, the flow can be stopped, which allows the pressure to build up inside accumulator or high-pressure hose 110 up to 8 psi. This allows high-pressure hose 110 to act as an accumulator where excess oxygen is stored in the compliance of this tubing while valve 108 is closed. Once valve 108 opens, this excess oxygen gas is released. If it happens quickly, all of the excess oxygen gas can be delivered during the inspiratory phase of patient P, which has the effect of increasing the effective $FiO_2$ as compared with the normal constant flow of oxygen.

In some embodiments, system 100 is configured to conserve oxygen. The present patent application proposes an improved way to deliver oxygen to patient P that is also using a non-invasive ventilator that minimizes the loss (waste) of oxygen.

In some embodiments, the present patent application was conceived and developed in response to the fact that an inspiratory-only delivery of oxygen from an Oxygen Blending Module (OBM) has nearly no application for home ventilation. This is because home ventilator patients use the oxygen concentrators, which use low-flow port 124, not the OBM. The primary issue with use of the oxygen concentrator is that it has a limited output ($FiO_2$), unlike the OBM, which provides all of the oxygen necessary to provide the user-specified $FiO_2$ (21-100%) up to very high flow rates. After understanding this actual oxygen concentrator need in the home ventilator, the present patent application was conceived and developed.

In some embodiments, ventilator 104 is configured to provide ventilatory support to patient P. In some embodiments, ventilator 104 includes a gas flow generator for providing a flow of gas to patient P and conduit 106 for delivery of the gas flow to an airway of patient P.

In some embodiments, ventilator 104 is configured to handle the software associated with turning valve 108 on and off, and a means of providing power to activate solenoid valve 108.

Figure 2:
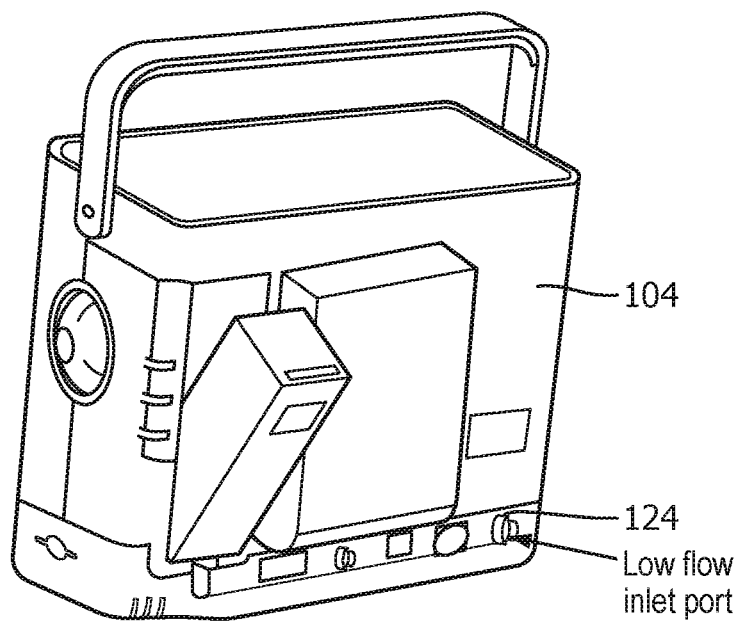
FIG. 2 shows an exemplary ventilator with a low-flow inlet port in accordance with an embodiment of the present patent application.
Figure 3:
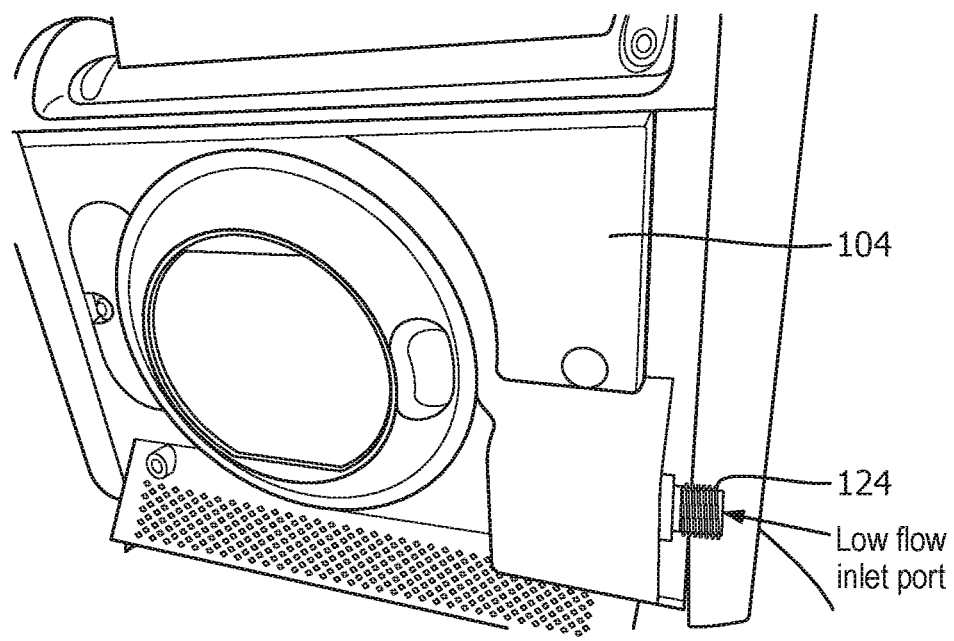
FIG. 3 shows an exemplary ventilator with a low-flow inlet port in accordance with another embodiment of the present patent application.

FIG. 2 shows pressure support ventilator 104. In order to supplement oxygen concentration in pressure support ventilator 104, some devices provide low-flow port 124 on the back of ventilator 104. FIG. 2 shows ventilator 104 with low-flow port 124. FIG. 3 shows another ventilator 104 with low-flow port 124.

Patient or breathing circuit 106 generally includes of an inhalation passageway and an exhalation passageway. The inhalation passageway is interconnected with ventilator outlet port enabling oxygen enriched air to be provided by ventilator 104 to patient P. Exhalation air is returned through exhalation passageway through ventilator return port to be exhausted into the ambient environment. In some embodiments, ventilator 104 is a portable ventilator.

In some embodiments, ventilator 104 may also be referred to as means for providing gas (to patient P through breathing circuit means 106). In some embodiments, the gas includes a mixture of air and the supply of oxygen from means 102 for supplying oxygen or oxygen source 102.

In some embodiments, oxygen source 102 is selected from the group consisting of an oxygen concentrator, a portable oxygen concentrator, a pressurized oxygen gas cylinder, a compressed oxygen gas cylinder, an oxygen generator, an oxygen blending module and an oxygen gas bottle. In some embodiments, reference numeral 102 is used to refer to any of the above-described oxygen sources.

In some embodiments, the oxygen generator is selected from the group consisting of a chemical oxygen generator, a membrane oxygen generator, a molecular sieve oxygen generator, and a ceramic oxygen generator.

In some embodiments, the oxygen blending module is a high-pressure oxygen blending module.

In some embodiments, oxygen source 102 may also be referred to means for supplying oxygen or means for providing oxygen.

In some embodiments, breathing circuit 106 is referred to as patient circuit, tubing, or circuit. As shown in FIGS. 2 and 3, ventilator 104 includes back surface that includes an air inlet that communicates with the gas flow generator, and oxygen inlet 124 that is selectively connectable to oxygen source 102.

System 100 includes one or more sensors 112. Sensor 112 is configured to measure breath flow information of patient P. In some embodiments, sensor 112 include a flow sensor for measuring breath flow information of patient P. In some embodiments, breath flow information is measured in units of Liters/seconds or Liters/minute. In some embodiments, sensor 112 include other sensor(s) or a combination of sensor as would be appreciated by one skilled in the art for measuring breath flow information of patient P.

Figure 7:
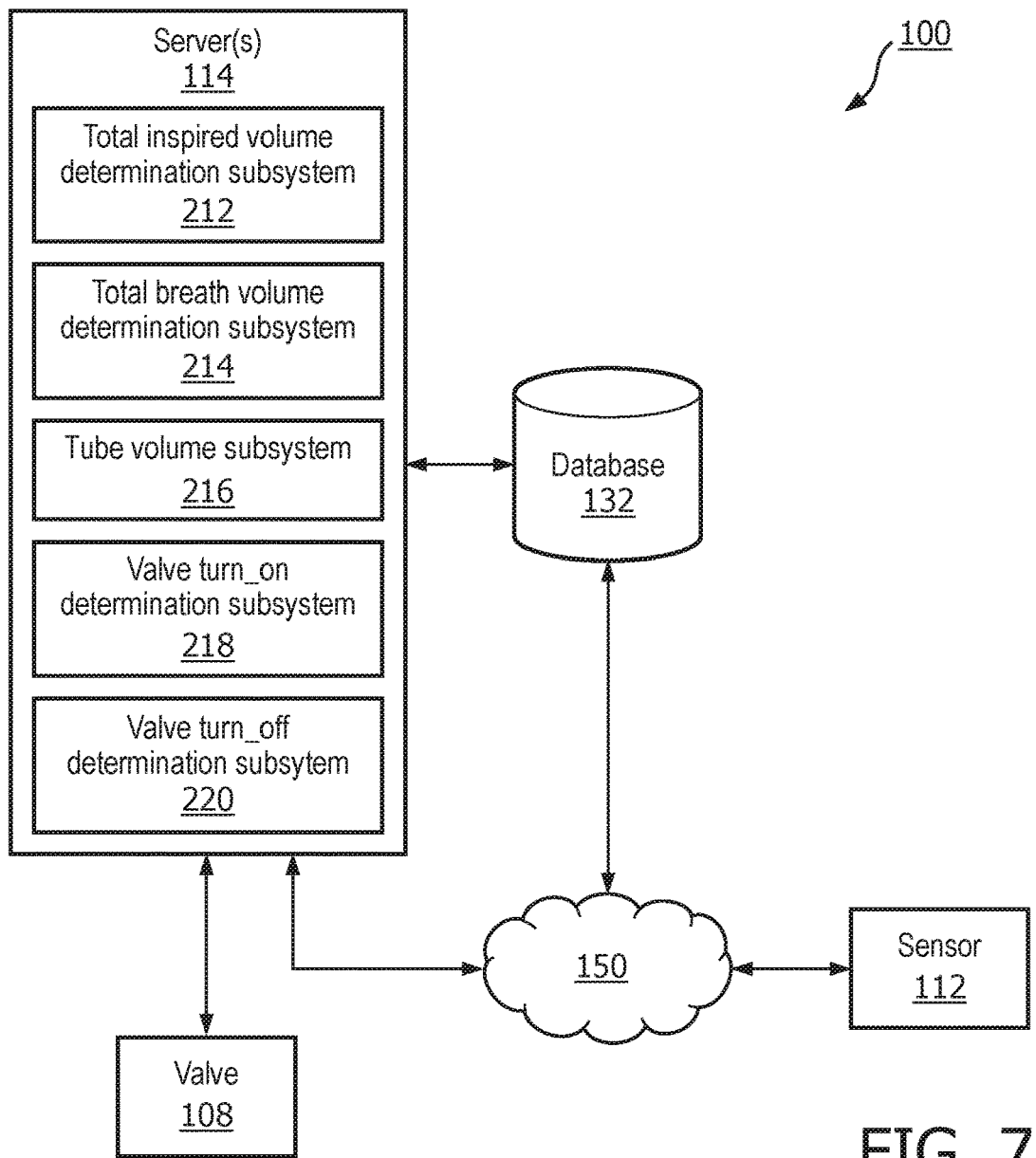
FIG. 7 shows an exemplary system for delivering oxygen to a patient in accordance with an embodiment of the present patent application.

In some embodiments, sensor 112 includes a transmitter for sending signals and a receiver for receiving the signals. In some embodiments, sensor 112 is configured to communicate wirelessly with computer system 114. As shown in FIGS. 1 and 7, in some embodiments, sensor 112 is configured to be operatively connected with one or more physical processors 116 of computer system 114. In some embodiments, sensor 112 is configured to communicate with ventilator 104. In some embodiments, sensor 112 is in communication with a database 132. In some embodiments, the breath flow information may be obtained from the database 132 that is being updated in real-time by sensor 112. In some embodiments, sensor 112 is in fluid communication with breathing or patient passage/circuit/tubing/conduit 106.

In one scenario, sensor 112 may provide the breath flow information to a computer system (e.g., comprising server 114) over a network (e.g., network 150) for processing. In another scenario, upon obtaining the breath flow information, sensor 112 may process the obtained breath flow information, and provide processed breath flow information to the computer system (e.g., comprising server 114) over a network (e.g., network 150).

In some embodiments, when valve 108 is in the open position, ventilator 104 is in fluid communication with oxygen source 102 such that the received supply of oxygen from oxygen source 102 is mixed with the ambient air within ventilator 104 to supply the desired fraction of inspired oxygen (FiO$_2$) during the inspiration phase of the breath cycle via breathing circuit 106 to the patient. In some embodiments, the breath cycle of patient P includes inspiration phase and expiration phase.

In some embodiments, when valve 108 is in the closed position, ventilator 104 is not in fluid communication with oxygen source 102.

In some embodiments, valve 108 is a solenoid valve. In some embodiments, valve 108 is a solenoid valve at low-flow port 124 of pressure support ventilator 104. In some embodiments, solenoid valve is used when oxygen source includes either an oxygen concentrator or an oxygen gas bottle.

In some embodiments, valve 108 is a servo valve. In some embodiments, valve 108 is a servo valve at low-flow port 124 of pressure support ventilator 104. In some embodiments, servo valve is used when oxygen source includes an oxygen blending module.

In some embodiments, solenoid valve 108 is controlled by ventilator 104 and located at the inlet of low-flow port 124 of ventilator 104.

In some embodiments, the open position of valve 108 may also be referred to as turn on position or as valve turn_on. In some embodiments, the closed position of valve 108 may also be referred to as turn off position or as valve turn_off. In some embodiments, valve 108 may also be referred to as an opening and closing means.

In some embodiments, accumulator 110 is operatively connected to valve 108, oxygen source 102, and ventilator 104. In some embodiments, accumulator 110 is a high pressure hose that is connected between valve 108 and oxygen concentrator 102.

In some embodiments, accumulator 100 typically has a length of high pressure hose that provides a conduit connecting oxygen concentrator 102 to valve 108. In some embodiments, other associated connectors on either end of this arrangement are necessary as well.

In some embodiments, accumulator 110 includes any container with any size, shape or volume. In some embodiments, accumulator 110 is selected based on the limit associated with the ability to charge and/or discharge accumulator 110 within the required time. In some embodiments, this would include a shorter hose or tubing with a larger internal diameter.

Figure 4:
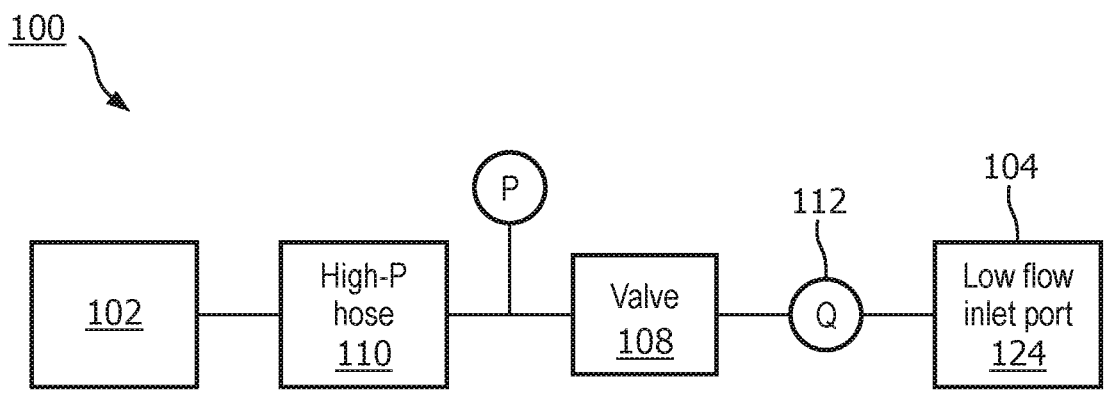
FIG. 4 shows an exemplary system for delivering oxygen to a patient in accordance with another embodiment of the present patent application.
Figure 5:
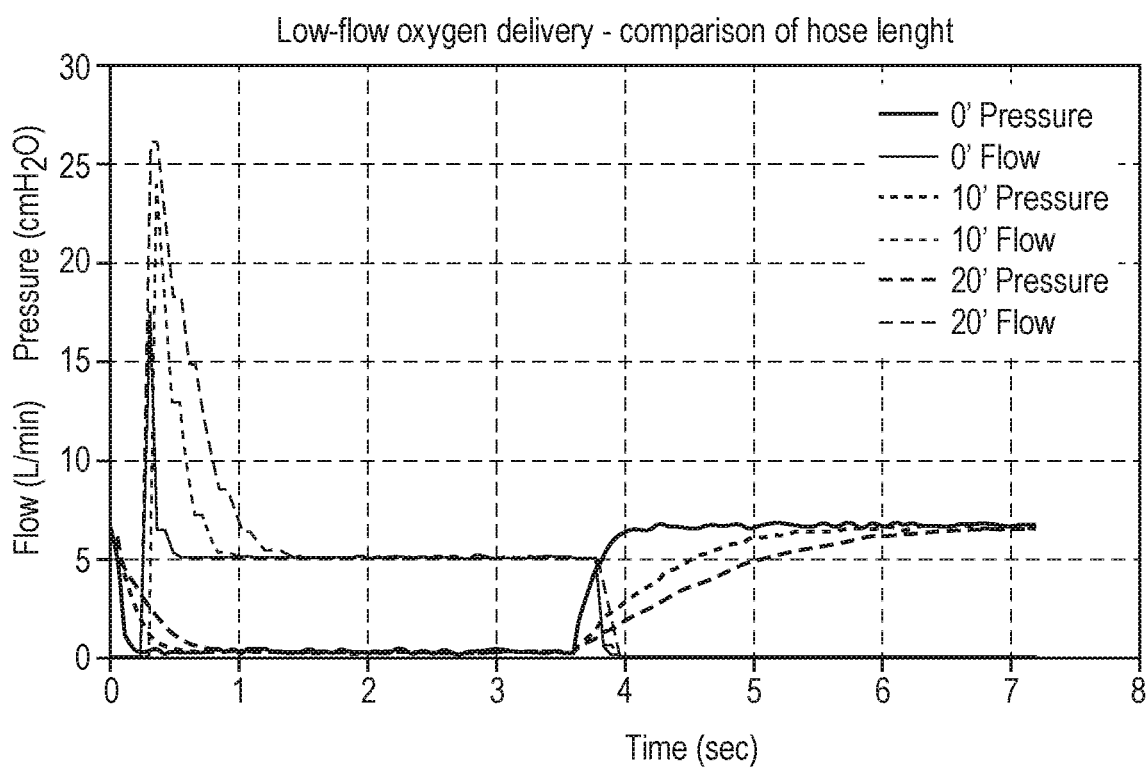
FIG. 5 is a graphical representation of flow and pressure measurements for various lengths of patient circuits in accordance with an embodiment of the present patent application.

FIG. 5 shows a graphical representation of data from an experiment in which oxygen concentrator 102 was set to deliver a constant oxygen flow of 5 Liters/minutes while valve 108 was closed for approximately 4 seconds and valve 108 was then opened for approximately 4 seconds in sequential cycles. The experimental set-up for collecting the data/information (as shown in FIGS. 5 and 6) is shown in FIG. 4.

In FIG. 5, the flow information/data for hose lengths of 0, 10 and 20 ft is shown as different dashed line (with levels of dash). The line pressure is also shown. From FIG. 5, it is evident that, as the hose length increases, delivered gas volume increases as does the circuit reload time.

FIG. 5 shows a graphical representation of low-flow oxygen delivery and comparison of pressure and volume data for various hose lengths (e.g., 0 feet, 10 feet, 20 feet). The pressure data and the flow data are shown on the left hand side Y-axis of the graph in FIG. 5. The pressure data is measured in centimeters of H$_2$0 (cm H$_2$0). The volume data is measured in Liters/minute (L/min). The time is shown on X-axis of the graph in FIG. 5. The time is measured in seconds.

Figure 6:
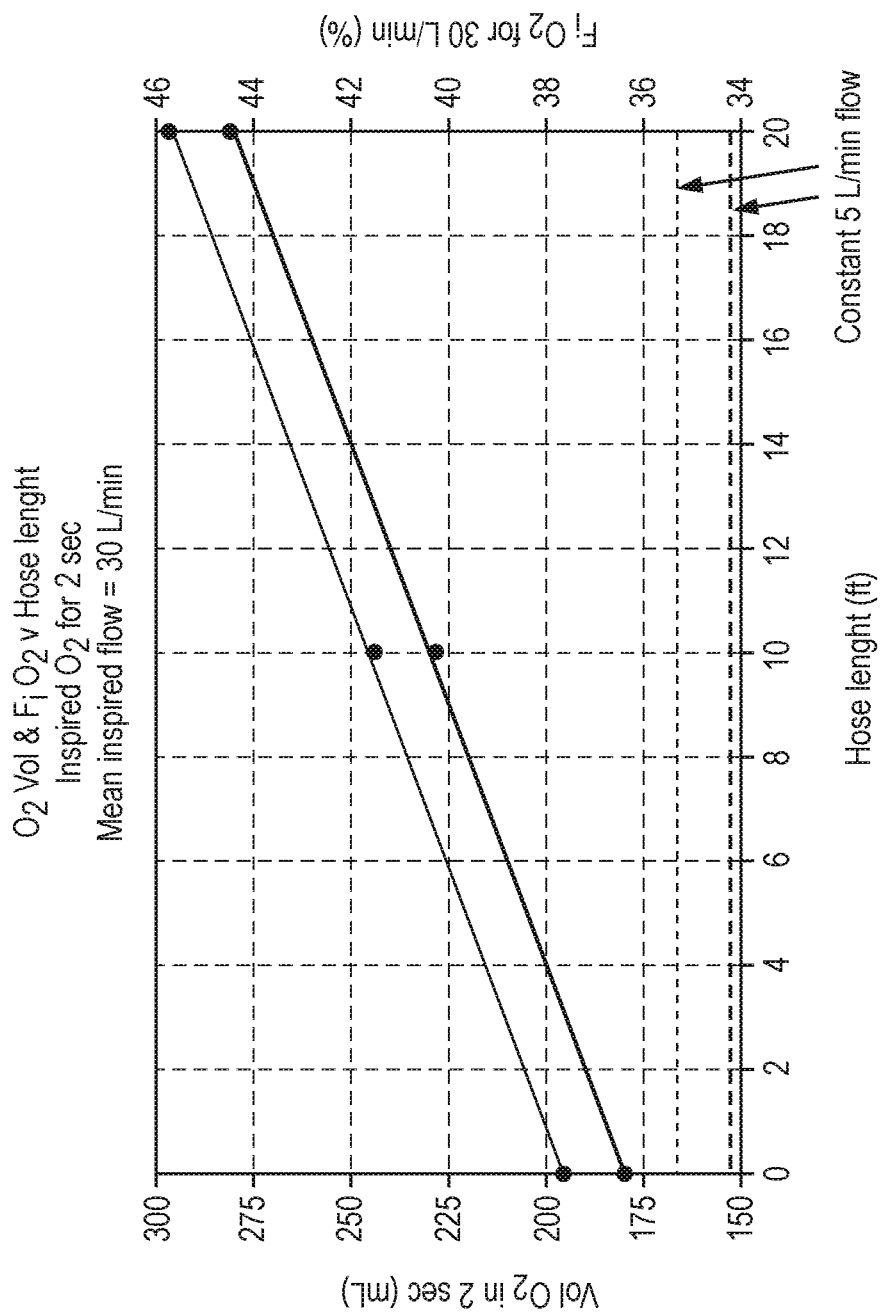
FIG. 6 is a graphical representation of delivered oxygen volume and expected $F_{io2}$ as a function of the length of patient circuit in accordance with an embodiment of the present patent application.

FIG. 6 shows a graphical representation of data from the same experiment (as referred to in FIGS. 4 and 5 and their related description above) as a measurement of oxygen volume with an estimation of FiO$_2$ for an inspiratory period of approximately 2 seconds, and an assumed inspiratory total flow of 30 liters/minute.

FIG. 6 shows a graphical representation of oxygen volume and FiO$_2$ for various hose lengths. The oxygen volume data for 2 seconds is shown on the left hand side Y-axis of the graph in FIG. 6. The oxygen volume data is measured in milliliters (mL). The FiO$_2$ data for 30 liters/minute is shown on the right hand side Y-axis of the graph in FIG. 6. The FiO$_2$ data is measured as a percentage value. The hose lengths are shown on X-axis of the graph in FIG. 6. The hose lengths are measured in feet.

The algorithm of the present patent application is a predictive algorithm that controls the use of valve 108 to deliver the pertinent gas into patient circuit 106 at ventilator 104 so that it appears at the patient-end of circuit 106 when patient P begins to inhale and stops when patient P stops inhaling.

The basis of this algorithm is that it uses volume measurements to decide when to deliver the gas rather than timing, which makes this algorithm much more robust. It is robust because such an algorithm is easy to implement and more accurate because it is less subject to noise since volume is obtained by integrating or summing flow rate (i.e., the process of integration always reduces noise in a system). Volumes are calculated by integrating the total flow during periods defined by the beginning or end of the inspiratory phase (e.g., called IEState) being delivered out of ventilator 104. Thus, the only continuous inputs to the algorithm are total ventilator flow and IEState. Additionally, the patient circuit volume (i.e., volume between the delivery point and patient P, also referred to as the tube volume) is also known or must somehow be indicated to the algorithm. The output of the algorithm is simply a signal when to turn on valve 108 that delivers the gas/oxygen, and when to turn valve 108 off.

Figure 19:
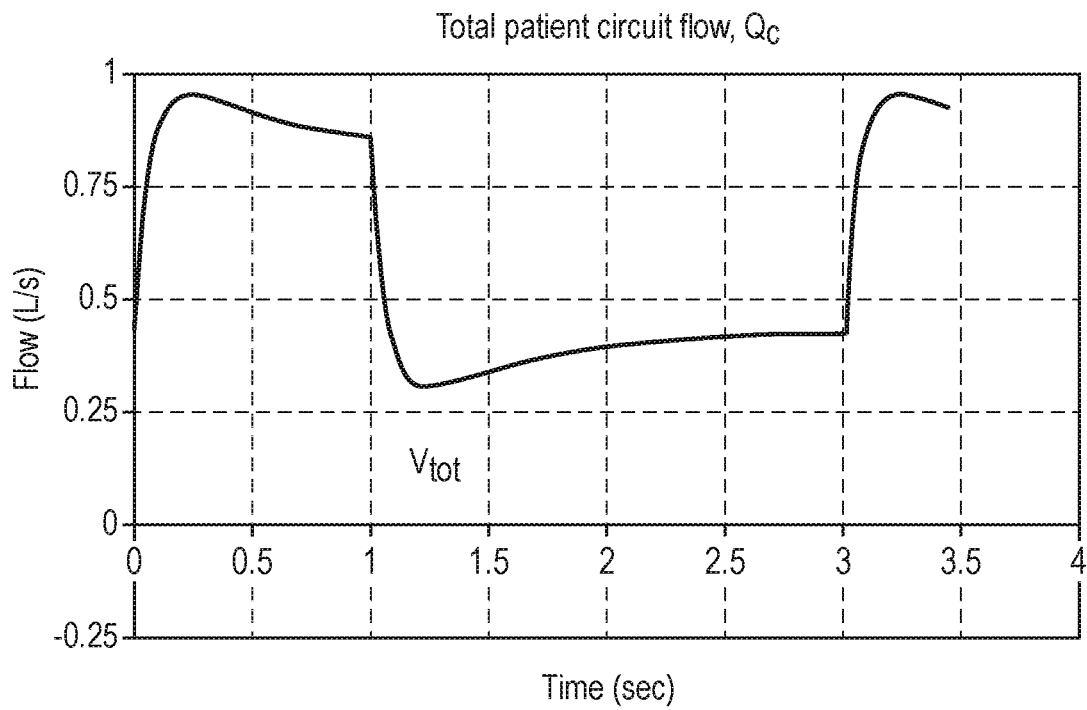
FIG. 19 shows an exemplary graphical representation of total patient circuit flow, where a location and quantification of the total breath volume, $V_{tot}$, for one breath cycle is shown, in accordance with an embodiment of the present patent application.
Figure 20:
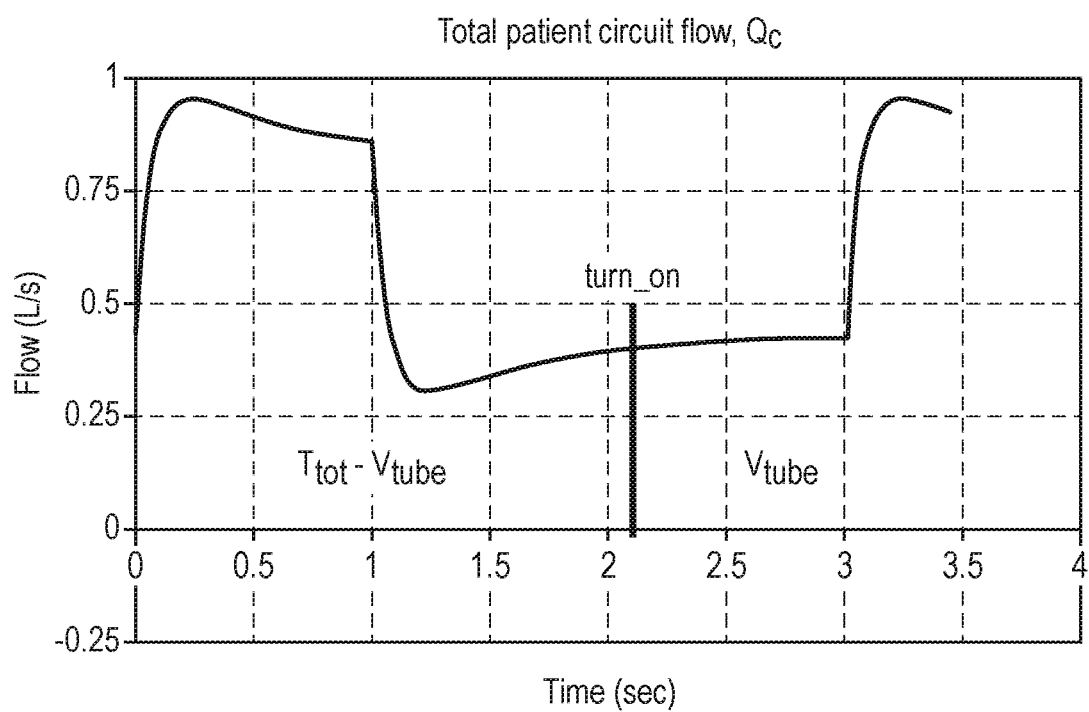
FIG. 20 shows an exemplary graphical representation of total patient circuit flow, where a volume encompassed by the difference between tube volume, $V_{tube}$, and total volume, $V_{tot}$ is shown, in accordance with an embodiment of the present patent application.
Figure 21:
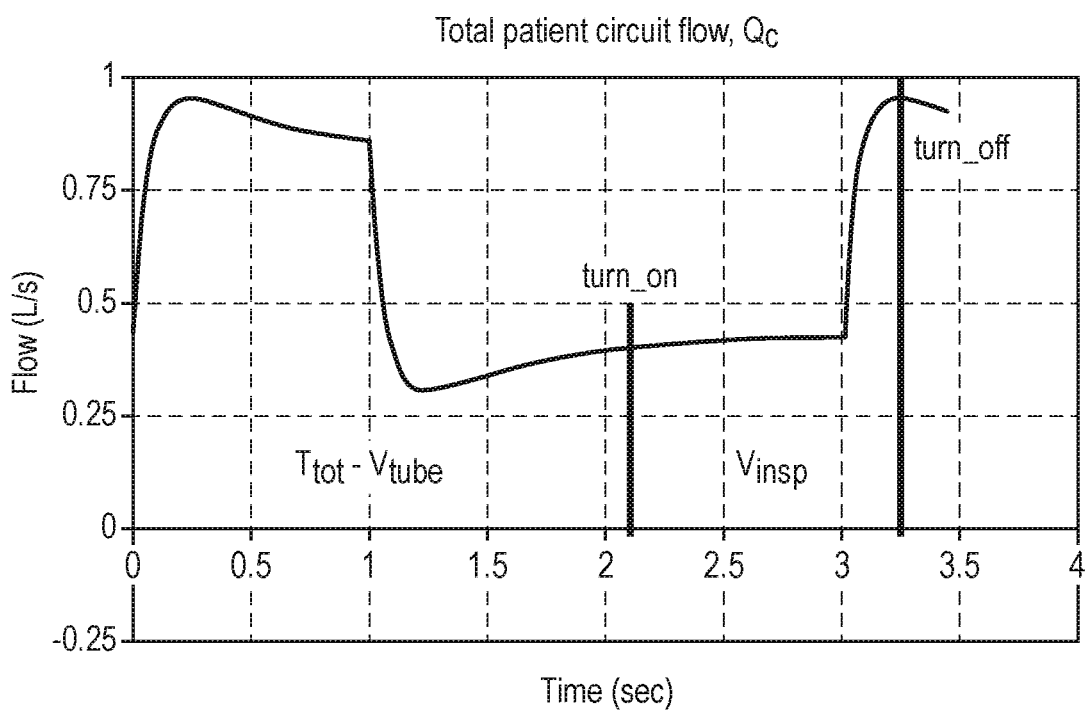
FIG. 21 shows an exemplary graphical representation of total patient circuit flow, in which delivery of the inspiratory volume, $V_{insp}$, is illustrated as starting at turn_on and stopping at turn_off, in accordance with an embodiment of the present patent application.

The algorithm works by calculating or knowing the following: 1) the total volume over one breath phase or cycle, $V_{tot}$ (see FIG. 19); 2) the total inspiratory volume by integrating from beginning to end of an inspiratory phase, $V_{insp}$ (see FIG. 18); and 3) the tube volume, $V_{tube}$ (e.g., input by the user or could be calculated by the ventilator—see FIG. 20). From there, a volume difference between $V_{tot}$ and $V_{tube}$ (see FIG. 20) is calculated and valve 108 is turned on when that volume difference ($V_{tot}-V_{tube}$) (see FIG. 20) is reached from the start of the next breath. As shown in FIG. 21, valve 108 is left open until $V_{insp}$ is delivered into tube 106 at which point valve 108 is closed or turned off. The algorithm is predictive meaning that it uses previous breath or breaths information to obtain the volumes to execute this algorithm. Also, there are a number of special cases that are described in detail below.

As shown in FIG. 7, system 100 for delivering oxygen to patient P may comprise server 114 (or multiple servers 114). In some embodiments, server 114 comprises total inspired volume determination subsystem 212, total breath volume determination subsystem 214, tube volume subsystem 216, valve turn_on determination subsystem 218, valve turn_off determination subsystem 220 or other components or subsystems. In some embodiments, tube volume, $V_{tube}$ is determined or calculated by system 100 and, in such an embodiment, tube volume subsystem 216 may be referred to as tube volume determination subsystem 216.

In some embodiments, server 114 comprises total inspired volume determination subsystem 212, total breath volume determination subsystem 214, valve turn_on determination subsystem 218, valve turn_off determination subsystem 220 or other components or subsystems. In some embodiments, tube volume, $V_{tube}$ received by system 100. That is, in some embodiments, tube volume, $V_{tube}$ input by patient P or user/caretaker/healthcare professional.

In some embodiments, total inspired volume determination subsystem 212 is configured to determine total inspired volume, $V_{insp}$. In some embodiments, total inspired volume determination subsystem 212 is configured to receive total flow signal, Q or breath flow information. In some embodiments, total flow signal, Q or breath flow information is provided to total inspired volume determination subsystem 212 by sensor 112. In some embodiments, total inspired volume determination subsystem 212 is configured to integrate the received total flow signal, Q or breath flow information to determine total inspired volume, $V_{insp}$. For example, determined total inspired volume, $V_{insp}$ is shown and described in detail with respect to FIGS. 18, and 21-22.

In some embodiments, total breath volume determination subsystem 214 is configured to determine total breath volume, $V_{tot}$. In some embodiments, total breath volume determination subsystem 214 is configured to receive total flow signal, Q or breath flow information. In some embodiments, total flow signal, Q or breath flow information is provided to total breath volume determination subsystem 214 by sensor 112. In some embodiments, total breath volume determination subsystem 214 is configured to integrate the received total flow signal, Q or breath flow information to determine total breath volume, $V_{tot}$. For example, determined total breath volume, $V_{tot}$ is shown and described in detail with respect to FIGS. 19-21.

In some embodiments, tube volume subsystem 216 is configured to determine tube volume, $V_{tube}$. In some embodiments, tube volume subsystem 216 is configured to receive tube volume information. In some embodiments, tube volume information is provided to tube volume subsystem 216 by one or more sensors associated with tube or patient circuit 106. For example, determined tube volume, $V_{tube}$ is shown and described in detail with respect to FIGS. 20-21.

In some embodiments, tube volume subsystem 216 is optional. In some embodiments, tube volume, $V_{tube}$ is input into system 100 by patient P or user/caretaker/healthcare professional. In some embodiments, tube volume, $V_{tube}$ that is input by patient P or user/caretaker/healthcare professional is received directly by valve turn_on determination subsystem 218.

In some embodiments, valve turn_on determination subsystem 218 is configured to determine when to turn on valve 108 or move valve 108 to its open position. In some embodiments, valve turn_on determination subsystem 218 is configured to calculate a volume difference between total breath volume, $V_{tot}$ and tube volume, $V_{tube}$. In some embodiments, valve turn_on determination subsystem 218 is configured to turn on (e.g., by sending a turn on signal to) valve 108 after the delivery of calculated volume difference (between total breath volume, $V_{tot}$ and tube volume, $V_{tube}$) from a start of a next breath cycle. For example, determined valve turn_on is shown and described in detail with respect to FIGS. 20-22.

In some embodiments, valve turn_off determination subsystem 220 is configured to determine when to turn off valve 108 or move valve 108 to its closed position. In some embodiments, valve turn_off determination subsystem 220 is configured to turn off (e.g., by sending a turn off signal to) valve 108 after the delivery of total inspired volume, $V_{insp}$. For example, determined valve turn_off is shown and described in detail with respect to FIGS. 21-22. That is, system 100 is configured to maintain valve 108 in the open position until the inspiratory volume of gas delivered to the patient during the inspiration phase of the breath cycle and provide the input to valve 108 causing the movement of valve 108 to the closed position after the inspiratory volume of gas is delivered to patient P.

In some embodiments, system 100 includes valve turn_on margin determination subsystem. In some embodiments, valve turn_on margin determination subsystem is configured to determine a margin for turning on valve 108. For example, determined valve turn_on margin is shown and described in detail with respect to FIG. 22 and also with respect to equations (20)-(23).

As will be clear from the discussions above and below, in some embodiments, system 100 includes computer system 114 that has one or more physical processors 116 programmed with computer program instructions that, when executed cause computer system 114 to obtain information or data from sensor 112. In some embodiments, computer system 114 may also be referred to as means 114 for executing machine-readable instructions with at least one processor 116.

In some embodiments, system 100 is configured to reduce oxygen waste using an oxygen blending module (OBM). The present patent application includes an algorithm that drives the oxygen blending module valve to allow delivery of gas so that it only enters the ventilator if it is going to be delivered to the patient during the inspiratory phase of the breathing cycle of patient P.

In order to supplement oxygen concentration in the pressure support ventilator, some devices provide an accessory oxygen blending module that allows high pressure gas to be plugged directly from a wall or bottled gas source into the ventilator. The function of the oxygen blending module is to use an onboard servo valve and flow meter, in conjunction with the ventilator system controls and measurement, to titrate the oxygen flow exiting the ventilator such that, within control error, it always has a user-specified $FiO_2$ residing somewhere between pure air at 21% and pure oxygen at 100%. FIG. 3 shows a rear view of ventilator 104 with the oxygen blending module (with its oxygen inlet port 124).

Such ventilators typically use passive patient circuits, in which there is a small hole in the circuit near the patient that allows gas from the circuit to exit directly to the room. The purpose of this hole is to remove $CO_2$-laden exhaled gas from the circuit. For supplemental oxygen users, this hole dumps a large percentage of per breath oxygen that is not consumed by the patient directly to the atmosphere.

The present patent application uses the on-board servo valve in the Oxygen Blending Module controlled by an algorithm, to shut off or greatly reduce oxygen flow during the expiratory phase of the patient. In this manner, oxygen waste can be greatly limited. For passive flow circuit applications, oxygen savings can be around 50%, and with active circuits, it can be up to 100%. It should also be noted that most patient circuits used are of the passive type (>80%), and that switching to an active circuit to enhance oxygen savings is clinically undesirable and a practice avoided at all costs. Thus, the real problem for oxygen waste in ventilators is with passive patient circuits.

When operating such an algorithm on a ventilator with an Oxygen Blending Module, it is important to also consider the effect of shutting off oxygen flow intermittently on both the ventilator alarms as well as the servo control system of the valve. It turns out that on the ventilator, controller 114 on the Oxygen Blending Module is fast enough that the setpoint for oxygen output from the ventilator can be changed even more than once per breath without significantly impacting the $FiO_2$ of the discharged gas when supplemental oxygen is released. The present patent application was conceived in response to complaints by clinicians of the problem regarding excessive waste of oxygen when using the ventilator. The present patent application reduces or eliminates oxygen waste when bottled gas is input to the Oxygen Blending Module of a pressure support ventilator, particular when being used with passive patient circuits. The present patent application includes an algorithm that controls shutting the Oxygen Blending Module valve (i.e., servo valve) on and off in order to substantially and predictively limit oxygen usage only during the inspiratory phase of patient P. The algorithm also takes into account the servo control system of the Oxygen Blending Module valve and any effects on alarms.

The present patent application is a software algorithm added to the ventilator to allow control of the Oxygen Blending Module valve (i.e., servo valve) with validation that normal operation whereby a controlled $FiO_2$ is still supplied when oxygen is being delivered. Because in the ventilators, the Oxygen Blending Module is an optional accessory, it is necessary for the software to be available when the Oxygen Blending Module is present in ventilator 104.

The present patent application includes an algorithm that functions in conjunction with the presence of an Oxygen Blending Module on ventilator 104. This device can be used on any ventilator that possesses an Oxygen Blending Module.

In some embodiments, system 100 includes a series of off-the-shelf parts or components that include a series of connectors, solenoid valve 108 with a pigtail wire that connects to ventilator 104, and a length of high pressure tubing 110. In some embodiments, software is also added to ventilator 104 to allow control of valve 108.

In some embodiments, system 100 includes any ventilator that possesses a low-flow oxygen inlet port and has a means of powering the associated solenoid valve 108 using on-board software.

The system of the present patent application that is used with bottled oxygen/gas as the oxygen source was conceived in response to the fact that an inspiratory-only delivery of oxygen from the Oxygen Blending Module (OBM) has nearly no application for home ventilation. This is because home ventilator patients use concentrators and sometimes bottled oxygen/gas, which use the low-flow port, not the Oxygen Blending Module. The primary issue with use of a gas bottle into low-flow port 124 is fast discharge of the bottle, which is expensive.

In some embodiments, system 100 is configured to reduce oxygen waste from bottled gas or gas bottle 102 supplying a ventilator low-flow gas mixing port 124. That is, system 100 is configured to reduce or eliminate oxygen waste when bottled gas 10 is input to low-flow port 124 of pressure support ventilator 104.

In one configuration, low-flow port 124 of ventilator 104 is supplied by high-pressure gas bottle 102. The problem is that most ventilator circuits are of the passive type, meaning that there is a constant leak from exhalation valve EV, resulting in that only a fraction of the oxygen delivered by ventilator 104 actually is inhaled by patient P. Most of the gas exits exhalation valve EV. Waste of bottled oxygen 102 is a problem due to the cost of charging and manipulating the bottles. It is therefore undesirable to use bottled oxygen with a low-flow port.

To at least in part solve this problem, the present patent application proposes placement of valve 108/a solenoid valve at low-flow port 124. In some embodiments, this valve 108 can be signaled and powered by an electrical port/connection on ventilator 104, or it could be just signaled by ventilator 104 while receiving power from some other source.

System 100 used with bottled gas 102 includes solenoid valve 108 that is ideally controlled by ventilator 104 and located at the inlet of low-flow port 124, and a length of high pressure hose/accumulator 110 that provides a conduit connecting gas bottle 102 to valve 108. Other associated connectors on either end of this arrangement are necessary as well. Ventilator 104 is also configured to be able to handle the software associated with turning valve 108 on and off, and a means of providing power to active solenoid valve 108.

In some embodiments, system 100 includes valve 108 operating in concert with the breathing phase of the patient via ventilator 104. In some embodiments, valve 108 is used to shut off the oxygen flow to ventilator 104. In some embodiments, the algorithm is used in ventilator 104 to drive valve 108 to allow delivery of gas so that it only enters ventilator 104 if it is going to be delivered to the patient during the inspiratory phase.

In some embodiments, accumulator 110/a high pressure hose is connected between this valve 108 and oxygen source 102/the gas bottle. Valve 108 is then turned on and off using the algorithm on ventilator 104 that ideally delivers the oxygen only during the inspiratory phase of patient P, who resides some distance away (e.g., usually at least 6 feet) from ventilator 104 and its attendant oxygen supply. In this manner, valve 108 is used to limit oxygen flow into patient circuit 106 so that supplemental oxygen only flows into patient P during inhalation and by default from exhalation valve EV, but only during the inspiratory phase, preventing the waste of oxygen from exhalation valve EV during the expiratory phase.

Because bottled gas is typically regulated to 50 psi, it may be ideal to limit the size of the connecting tube volume as much as is practicable so that it does not charge significantly when valve 108 is closed. In this manner, the 50 psi charge that will fill the tube 110 when valve 108 is closed will be limited in volume, allowing the gas flow setting on the rotameter to be more accurate. However, the rotameter setting can also be titrated down to account for the tubing charge in order to limit oxygen waste while still providing the same effective $FiO_2$, but delivered at a lower indicated gas flow from bottle 102.

When using a passive flow circuit, the oxygen savings can be up to 50%, which is certainly significant. For active circuits, oxygen savings can be 100% (the only oxygen delivered goes only into the patient during inhalation).

In some embodiments, system 100 includes a series of off-the-shelf parts or components that include a series of connectors, solenoid valve 108 with a pigtail wire that connects to ventilator 104, and a length of high pressure tubing 110. In some embodiments, software is also added to ventilator 104 to allow control of valve 108. In some embodiments, system 100 includes any ventilator that possesses a low-flow oxygen inlet port (e.g., 124) and has a means of powering the associated solenoid valve 108 using on-board software.

Figure 8:
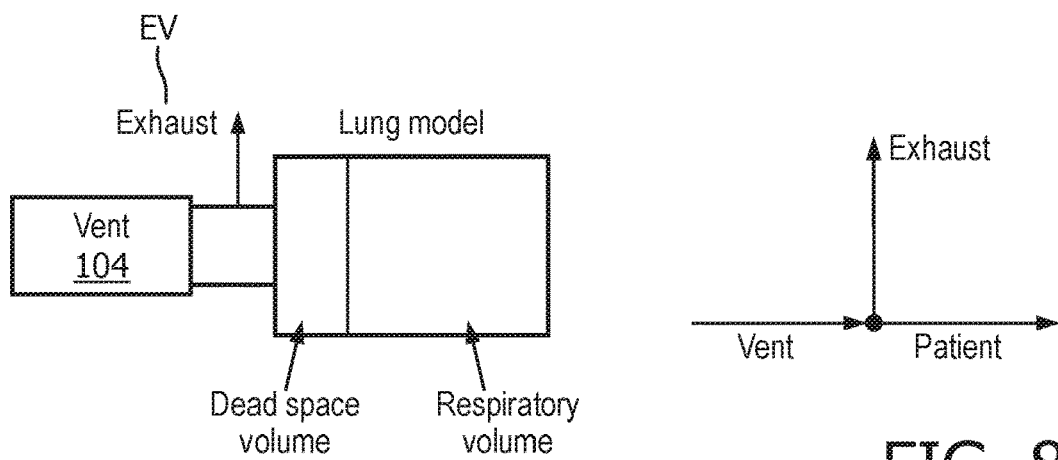
FIG. 8 shows an exemplary model of a ventilator, an exhaust valve and a lung showing anatomic deadspace volume in accordance with an embodiment of the present patent application.

In the following analysis, a model was developed and used. This model of breathing that describes the logic associated with when supplemental oxygen is needed in the gas flow stream to the lungs and when it is not. A simple ventilator, exhalation valve and lung model are presented in FIG. 8. FIG. 8 shows anatomic deadspace volume. In this model, the following assumptions were made: 1) supplemental oxygen can be added (or ceased) precisely into the airstream emanating from the ventilator; 2) there is some known leak from the exhaust valve; 3) the lung has a certain volume, $V_T$, and it is comprised of ⅓ anatomical deadspace at the connection to the patient circuit; and 4) for the sake of simplicity, there is no volume between the ventilator and the lung. This allows one to consider the system with gas entering and exiting the lung where the oxygen can be turned on and off as precisely needed at the mouth, without having to consider volume located between the ventilator and the lung.

Figure 9:
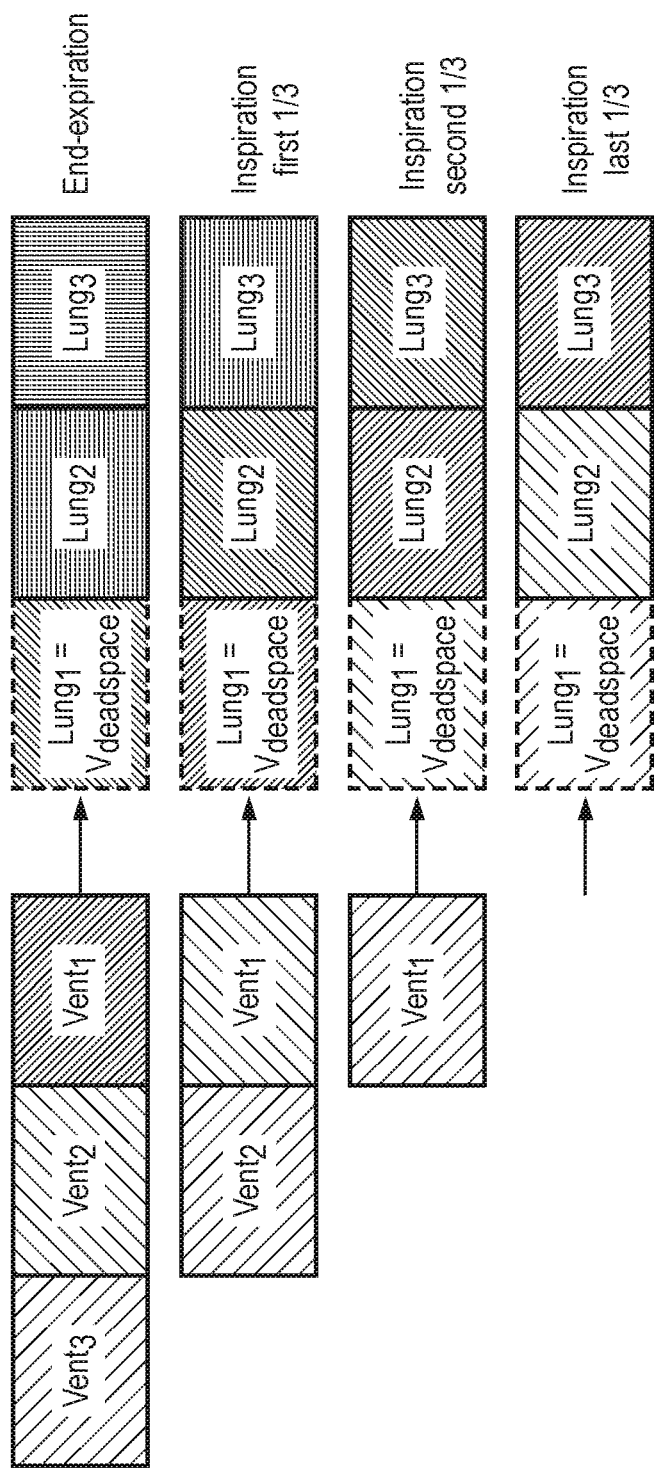
FIG. 9 shows an exemplary representation of insertion of fresh gas from the ventilator into the lung during one inspiration phase in accordance with an embodiment of the present patent application.

In considering this model, the state of gas in the lungs and circuit during the various phases of breathing are reviewed. FIG. 9 shows an insertion of fresh gas from the ventilator into the lung during one inspiration phase and assists in this analysis. Color depth in FIG. 9 only indicates the location of each one-third gas bolus relative to its start location in the first row. The first row illustrates the lung state at the end of expiration. The three blocks on the left are three ⅓ $V_T$ boluses of ventilation air that will enter the lung on the right, which is broken into three volumes also. Each row after that indicates movement of a third of the ventilator gas into the lung. Note that the gas already in the lung does not go away, it is just indicated as being replaced by the fresh gas.

FIG. 9 illustrates precisely where the volume delivered by each breath cycle is delivered during the inspiratory phase. This allows one to have a clear understanding of exactly what fractions of delivered gas require full supplemental oxygen.

The type of gas and its location during each phase of breathing are reviewed in detail next. This analysis requires considering that gas moves in boluses throughout the system. This means that the mixing of gas along the airflow path are not considered and that gas concentrations are preserved as they move along the ventilation path.

Before the start of inspiration, the anatomic deadspace is filled with gas containing the poorest quality inspiratory air (i.e., most oxygen depleted and highest $CO_2$ content) as shown in FIG. 9. This means that the first phase of inspiration (inspiring bad air) is inhalation of a volume of gas that is of the poorest inspiratory quality and has a volume equal to anatomical deadspace. Because of this, it is important that the gas from the ventilator (i.e., that just outside of this anatomic deadspace—"$Vent_1$" in FIG. 9) contains the desired oxygen content.

The anatomic deadspace is lastly filled with fresh breathing gas, and not only does it not take part in gas exchange, it is exhaled and removed from the ventilation circuit. This volume is therefore a major source of oxygen waste because it is not involved in ventilating the patient but is dumped directly to the atmosphere.

Only the first ⅔ of each inhaled tidal volume actually aids gas exchange by providing fresh gas. The first ⅓ of the inhalation into the lung is poor quality gas residing in the anatomic deadspace that is left behind from the previous exhalation phase, then the first ⅔ of the inhaled tidal volume becomes the last ⅔ of inhalation into the lung. Lastly, the last ⅓ of $V_T$ is not involved in gas exchange as it only goes to fill the anatomic deadspace.

During exhalation, all of the tidal volume is exhaled through the exhalation valve unless there is re-breathing. During exhalation, if the flow of exhaled gas exceeds the ability of the leak valve to exhaust it, gas will be pushed backwards through the ventilator until the leak valve flow once again exceeds the patient exhalation flow. Thus, any supplemental oxygen that is entrained into the patient circuit will exit backward through the ventilator at this time and will therefore be wasted. Lastly, regarding the exhalation valve, whatever type it happens to be, any oxygenated gas exiting the valve is wasted.

Given these considerations, the algorithm of the present patent application has the following goals 1) do not inject oxygen during retrograde flow back up the patient circuit; 2) do not add oxygen into the final ⅓ of $V_T$ representing anatomic deadspace; 3) do not add oxygen during the expiratory phase; 4) minimize oxygen that simply exits the exhaust valve; and 5) make sure that there is fully oxygenated gas at the very beginning of inspiration.

In descriptions of the algorithm (referring to FIG. 9) in the present patent application, a theoretical gas usage of ⅖ or 22% (e.g., see equation 4) of that used without the algorithm if a] a passive exhalation patient circuit is used and b] anatomic deadspace is not enhanced with the delivered gas (representing the final ⅓ of a breath). Also, in descriptions of the algorithm in the present patent application, the model shows a savings of 30-70%, with an assumed average of 50%. These two cases may not seem incompatible as the latter model does not assume that gas is not delivered into the anatomic deadspace as is the case with the first model. The reason is that the latter model was derived with humidity delivery in mind, in which case the deadspace would be absolutely humidified. In the former model, the goal was oxygen supplementation, whereby delivery of gas into the anatomic deadspace is wasteful and an opportunity for savings. This distinction between the two models is provided here to reconcile the differences between the two models.

Figure 10:
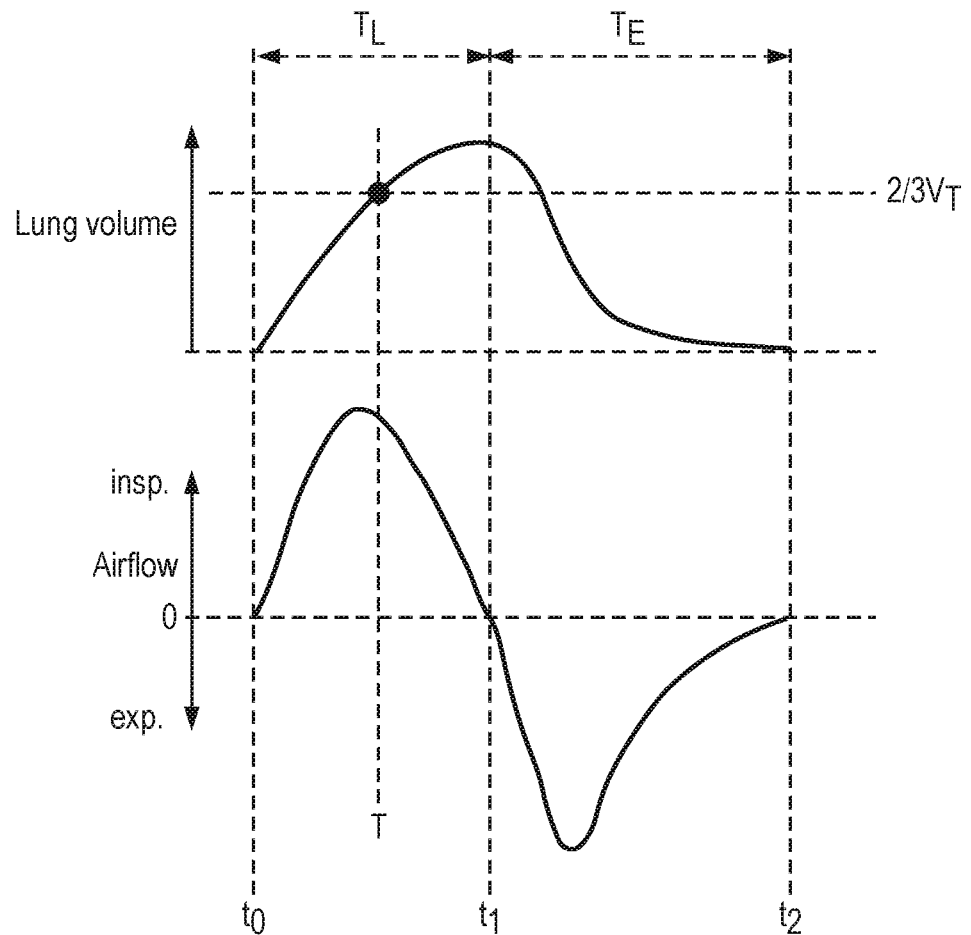
FIG. 10 shows volume and flow traces for one breath in accordance with an embodiment of the present patent application.

FIG. 10 is used to develop the math associated with the algorithm of the present patent application. FIG. 10 shows volume and flow traces for one breath cycle. The dot in FIG. 10 indicates the location of ⅔ of $V_T$.

It is apparent from the information given above that supplemental oxygen must be in full flow at the beginning of inspiration, and must continue until at a minimum, ⅔ of tidal volume has been inhaled. The only resulting waste of oxygen will be that which exits the exhaust valve during this period. This can be written in the form of following equation (1):

$$\text{Min Time } O_2 \text{ ON: } \int_{t_0}^{T} Q_L + \tfrac{2}{3} V_T \qquad \text{Equation (1)}$$

where $V_T$=tidal volume; and
$Q_L$=flow from the exhalation valve; and
T=period during which ⅔ $V_t$ is delivered; and
$t_0$=breath start time It is apparent then that supplemental oxygen should be off for the remainder of the time over the full breath cycle, which can be written in the form of the following equation (2):

$$\text{Time } O_{22} \text{ OFF: } \int_{T}^{t_2} Q_L + \tfrac{1}{3} V_T \qquad \text{Equation (2)}$$

where $V_T$=tidal volume; and
$t_2$=breath end time.

An estimate of maximum theoretical oxygen savings is to be determined when there a constant oxygen flow. The analysis is simplified by assuming that leak flow is constant during the entire breath cycle. If an oxygen concentrator is used, the oxygen flow, $Q_{O_2}$, is effectively constant during operation of the ventilator. This makes calculation of the oxygen savings easy. For normal operation, the oxygen volume used per breath is be calculated as shown in equation (3a) below.

$$V_{O_{2_{normal}}} = Q_{O_2}(t_2 - t_0) = Q_{O_2}(T_I + T_E) \quad \text{Equation (3a)}$$

where $Q_{O_2}$=oxygen flow $V_{O_{2_{normal}}}$

=oxygen volume per breath;
$(t_2-t_0)$=breath period measured as the difference between breath end time and breath beginning time; and
$(T_I+T_E)$=breath period measured as the sum of inspiratory and expiratory time.

With the algorithm as defined in (1) and (2), the oxygen volume used per breath is given as shown in equation (3b) below:

$$V_{O_{2_{OWL}}} = Q_{O_2}(T - t_0) \quad \text{Equation (3b)}$$

where $V_{O_{2_{OWL}}}$

=oxygen volume used per breath.

If it is assumed that the inspiratory phase can be approximated by a square wave (constant flow), then the oxygen flow period, $(T-t_0)$, represents exactly ⅔ of the inspiratory phase. Furthermore, for an I:E (i.e., inspiratory:expiratory ratio) of 1:2, oxygen on-time is ⅔ of ⅓ of the total breath period. This means the oxygen volume can be represented using equation (4) below.

$$V_{O_{2_{OWL}}} = \frac{2}{9} V_{O_{2_{normal}}}, \quad \text{Equation (4)}$$

where $V_{O_{2_{normal}}}$

=oxygen volume used per breath in the absence of the algorithm.

This is indeed a huge potential savings of oxygen.

Figure 11:
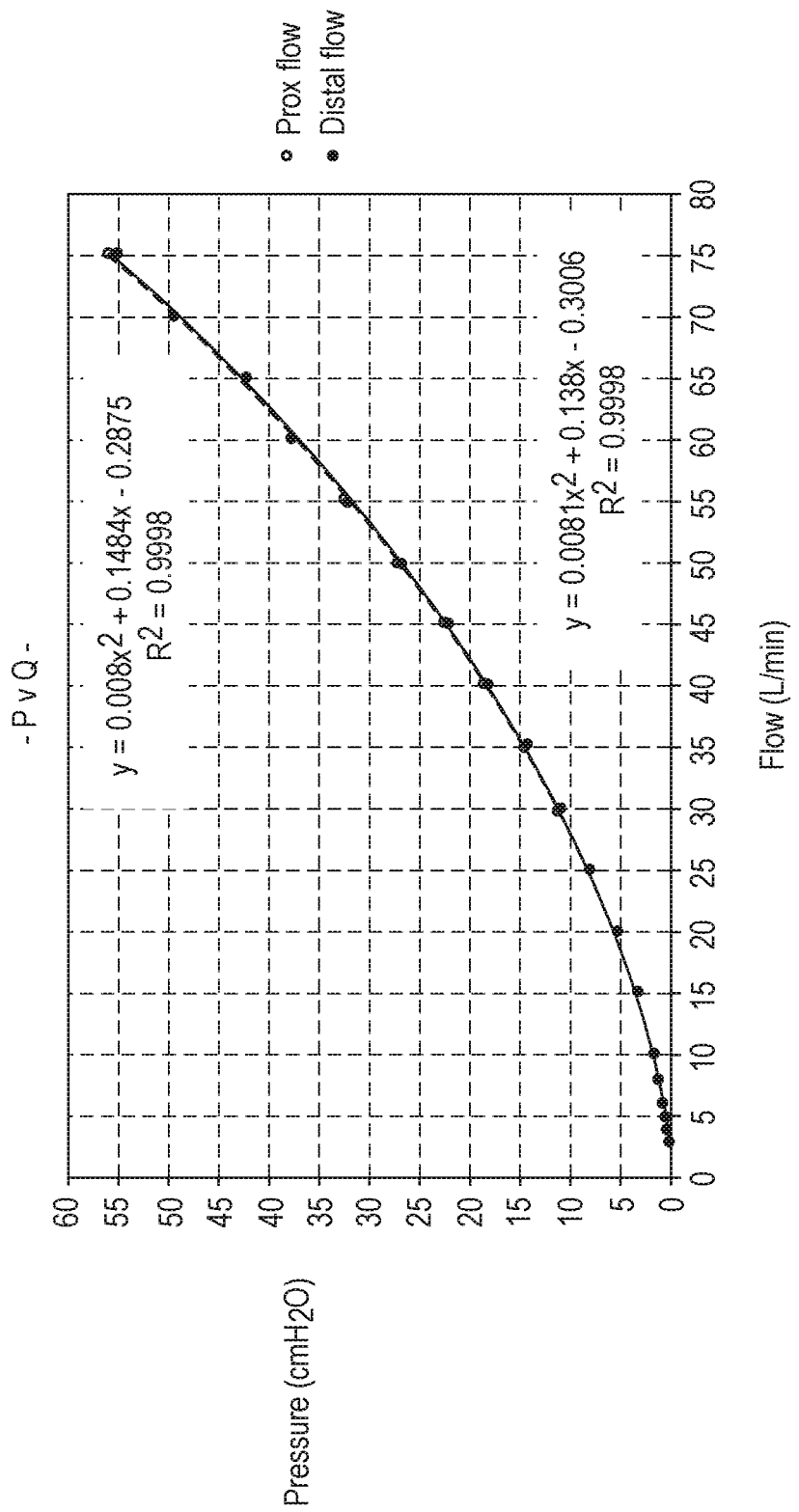
FIG. 11 shows pressure vs flow curve in accordance with an embodiment of the present patent application.

The overall goal of the algorithm when using the passive flow circuits is to minimize supplemental oxygen from exiting exhalation valve EV. To assess the amount of gas that exits exhalation valve EV during operation, flow versus pressure curve of exhalation valve EV is used. FIG. 11 shows a graphical representation of flow versus pressure curve of exhalation valve EV. The pressure data is shown on the left hand side Y-axis and the flow data is shown on X-axis of the graph in FIG. 11. The pressure data is measured in centimeters of $H_2O$ (cm $H_2O$). The volume data is measured in Liters/minute (L/min).

Forward and backward flow curve-fits are averaged to obtain equation (5) below.

$$\Delta P = 0.008 Q^2 + 0.148 Q - 0.290 \quad \text{Equation (5)}$$

where Q=EV flow; and
P=EV pressure

Using the quadratic formula, equation (5) is inverted to be able to calculate flow as a function of pressure. This results in equation (6) below.

$$Q = -8.94 + \sqrt{116.13 + 125.0 \Delta P} \quad \text{Equation (6)}$$

A series of flows are calculated to illustrate the flows from exhalation valve EV and are presented in the table shown in FIG. 12. The table in FIG. 12 shows exhalation valve EV's flows versus circuit pressure. It can be seen from the table in FIG. 12 that the volume leaked from the valve during 2 seconds at the given pressures is very high. Moreover, it should be noted that even with the best algorithm, it is not possible to shut off the exhaust flow EV during the inspiratory phase, where the gas must be oxygenated. Considering this and observing the table in FIG. 12, the algorithm still results in significant oxygen loss.

The difficulties associated with trying to reduce oxygen with a passive flow circuit are also further pointed out. Keep in mind that in order to turn on and shut off oxygen as directed by equations (1) and (2) above, the primary hurdle is that the trigger and cycle times must be predicted given that the gas concentrations must be correct at patient P, but they are administered at ventilator 104, with a 700 mL patient circuit intervening. Other questions include: 1) what is the basis of an algorithm where oxygen flow must be turned on and off with the intervening patient circuit? 2) how to address exhaled gas traveling back up the patient circuit at the beginning of expiration? 3) how is oxygen delivery affected by mask leak? 4) how to address variable breathing volumes? 5) how to address variable breath rates? 6) what is the realistic effect of diffusive mixing at the bolus interfaces? 7) how does tube curvature/orientation affect mixing while gas travels in the circuit? 8) What is the limit of such an algorithm as tidal volume decreases to pediatric levels? Given all of these difficulties, other options were looked at before trying to develop an algorithm for the passive flow circuits.

The first option that was looked at is the active flow circuit. On its face, there was a much greater opportunity to improve the oxygen waste problem, simply because there is no exhaust flow during inspiration. During exhalation, moreover, there is a dump phase where the active exhalation valve (AEV) is opened wide, resulting in strong exhalation from the patient, but also flow loss from the ventilator. The magnitude of volume lost from the ventilator during the dump phase is not actually known, but it is likely highly variable and could be very large.

The dump phase is followed by a continuous "bias" flow from the ventilator that exits the active exhalation valve for the remainder of the exhalation phase. Bias flow is targeted to be around 10 L/min, which results in a volume loss of only 0.33 L for 2 seconds of flow, substantially lower than the values given in the table in FIG. 12.

Figure 13A:
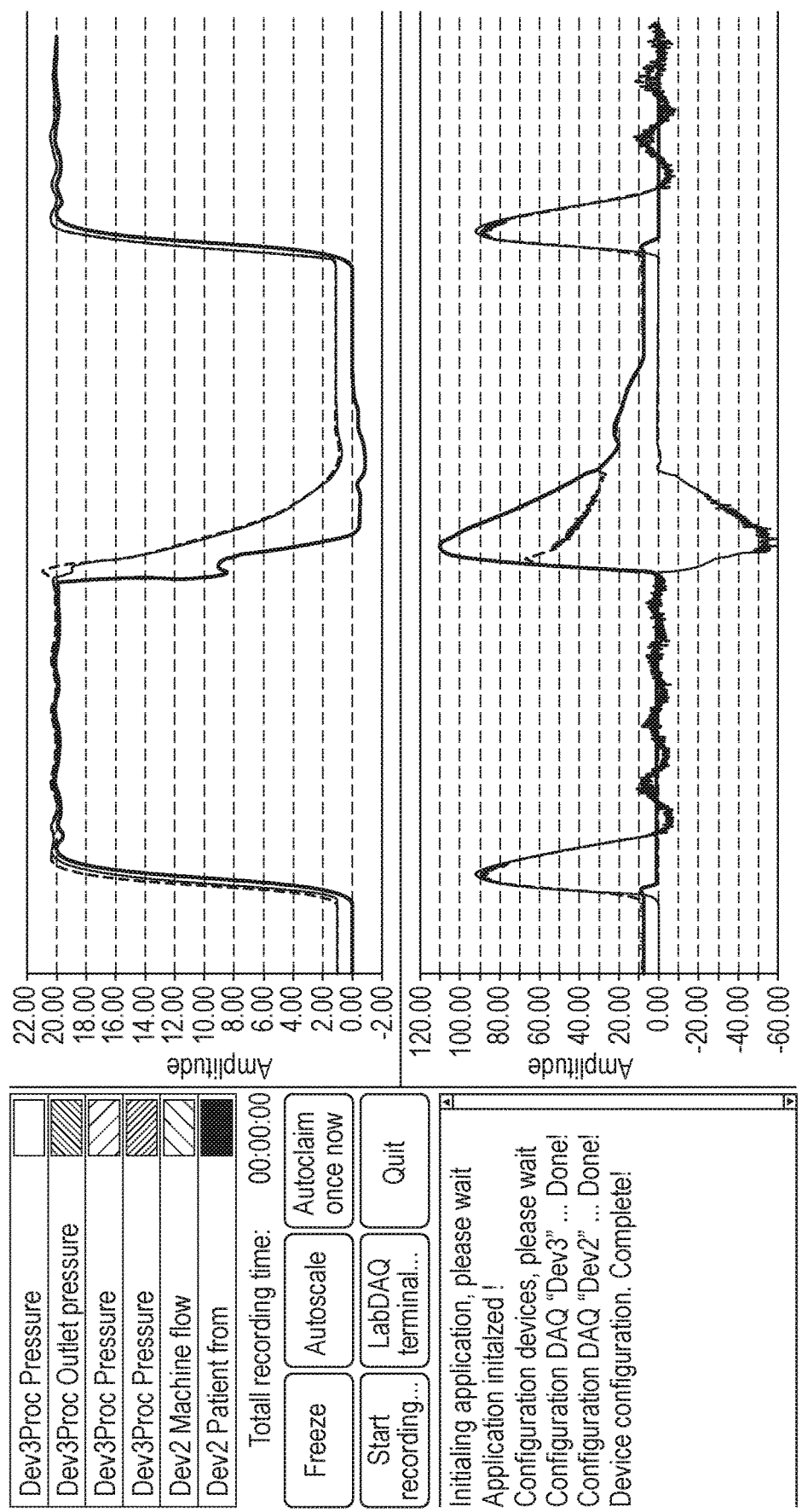
FIGS. 13a-13c show dump flow and bias flow in accordance with an embodiment of the present patent application.
Figure 13B:
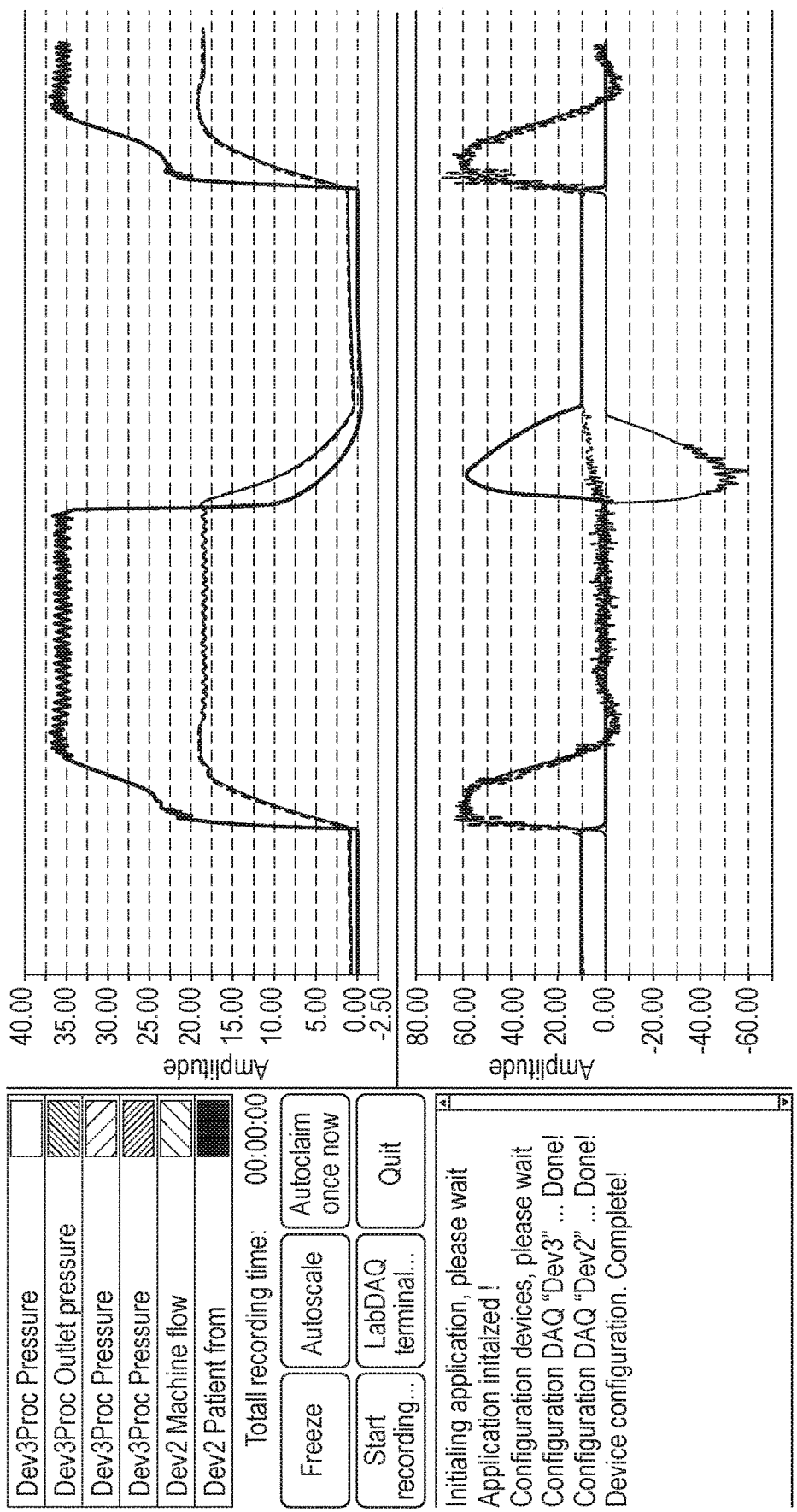
Figure 13C:
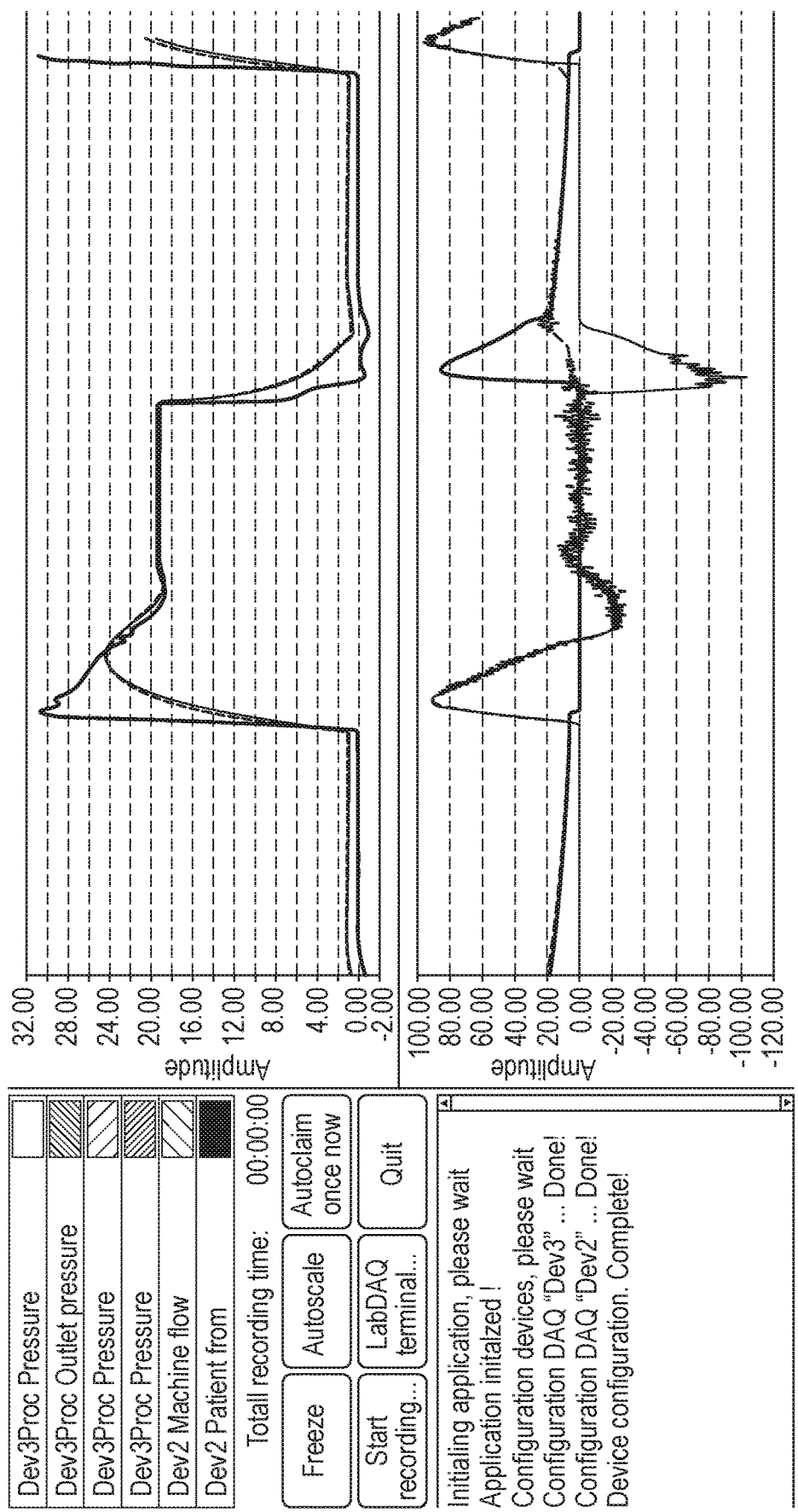

The dump and bias flow phases are reviewed in more detail using FIGS. 13a-13c. Three ventilators on a number of different active exhalation valve options were used to review the dump and bias flow behaviors. Similar behavior for both dump and bias flow was observed with all three ventilators on a number of different active exhalation valve options. FIGS. 13b-13c show that they both have essentially no excess vent flow during the dump phase and that the flow magnitude changes from that at end-inspiration (e.g., nearly 0) to the bias flow level. FIG. 13a, on the other hand, shows that it has a large blast of ventilator flow that exits the active exhalation valve during the dump phase.

The key advantage to the active flow circuits is that exhaust flow is 0 during the inspiratory phase, which would result in no oxygen waste. Moreover, from observing FIGS. 13a-13b, it can be seen that it is possible for ventilators to control the dump flow to minimize or frankly vent flow and its attendant oxygen. Also, because the magnitude of the bias flow that is controlled, it should be possible to limit this flow even further than 10 L/min in the algorithm. In summary, the algorithm using an active flow circuit benefits from the following: a) no loss of oxygen during the inspiratory phase, a benefit that already exists with active circuits (no additional algorithm necessary) b) vent (oxygen) flow during the dump phase can be reduced or eliminated c) bias flow can be adjusted as low as possible; and d) the benefits of the algorithm with the active flow circuits is the same for active PAP or active flow.

There is another potential method to improve oxygen wastage during the dump and bias flow, which is to develop an algorithm that shuts off the oxygen in anticipation of the exhalation phase. This is similar in principle to what was considered above for the passive valve, and it has many of the same problems, but such an approach would allow dump control and bias flow to remain as they are. Such an approach would allow us to address not filling the last third of the title volume with oxygen in the anatomic deadspace.

In the below sections of the present patent application, the initial time-based algorithm is presented, along with the volume-based algorithm and the special cases that are addressed.

This problem is fairly complex because it involves compensating for the volume of the patient circuit tubing residing between the patient and humidifier. This necessitates predicting the timing in advance required to engage the humidifier so that humid air is present at the patient airway when inhalation starts. Obviously, it is impossible to predict this precisely because the on-time of the humidification process must actually be predicted, but there are assumptions one can use to facilitate this prediction, and the algorithm can always fall back to continuous delivery of humidification as a default. These assumptions are delineated below.

Figure 14:
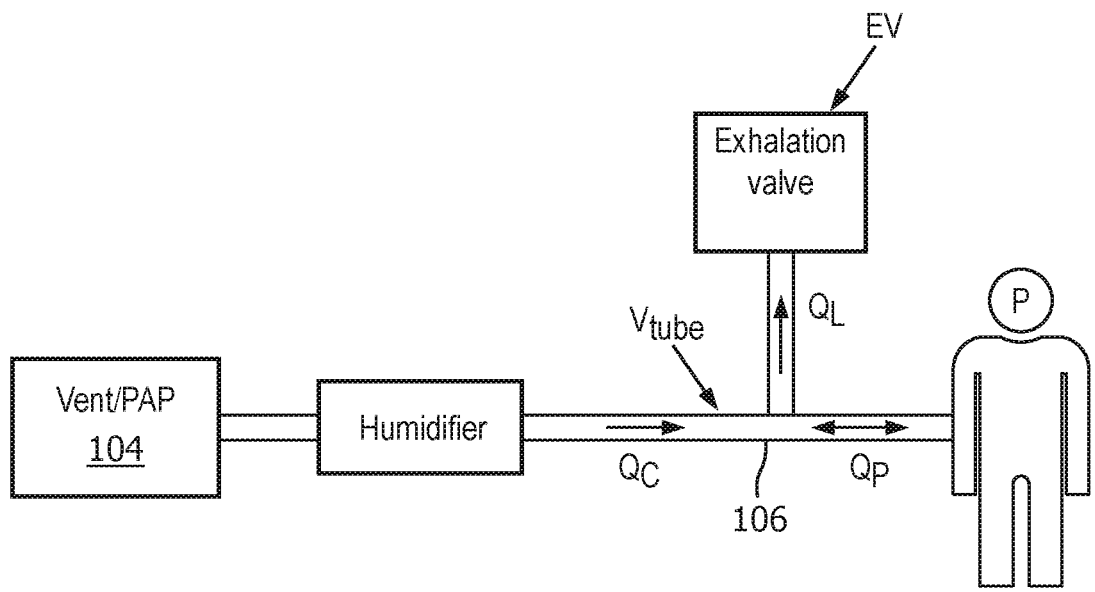
FIG. 14 shows an exemplary schematic of patient circuit hardware and flow paths in accordance with an embodiment of the present patent application.

FIG. 14 depicts a flow circuit model that is used as the basis of the algorithm. A number of approaches that centered on calculating volume associated with the different flows in the patient circuit were attempted. Calculating volume itself is straightforward, but it becomes complex in the presence of the constant leak flow exiting the system. The reason is that volume is the continuous integral of the flow signal summed over time. With a constant leak, however, the integral always tends toward infinity, thus requiring one to choose a time or condition in which to reset it.

In addition to difficulties associated with calculating volumes, there are a number of other complexities related to other aspects of the system model that require some attention. These complexities initially motivated us to consider implementing only the most simple version of the model depicted in FIG. 14. The list of these conditions is given here: 1) patient breathing profile is in a sine wave; 2) peak exhaled flow magnitude does not exceed leak flow (no retrograde flow in the patient circuit); 3) constant breath rate and minute volume; 4) constant leak flow—patient use of CPAP.

More sophisticated operation was then included in the model as it became more developed. The sophisticated operation of the model included 1) patient exhaled flow magnitude exceeds leak flow; 2) use of bi-level pressure and its implications for both leak and the more complex breath pattern; 3) patient breath pattern based on the first-order filtered rise and fall times with appropriate I:E; and 4) how to deal with changing breath rate and tidal volume.

After evaluating various volume methods unsuccessfully, an approach based almost exclusively on timing was devised. This approach requires a single finite integration of flow to assess the timing associated with tube volume, $V_{tube}$. Before describing the detail of the algorithm, an important aspect of this model that relates to volume calculations is first addressed. The expression for flow illustrated in FIG. 14 is as shown in the equation (7) below.

$$Q_C(t)=Q_L(t)+Q_P(t) \qquad \text{Equation (7)}$$

where $Q_C$=total circuit flow;
$Q_L$=leak flow; and
$Q_P$=patient flow

Figure 15:
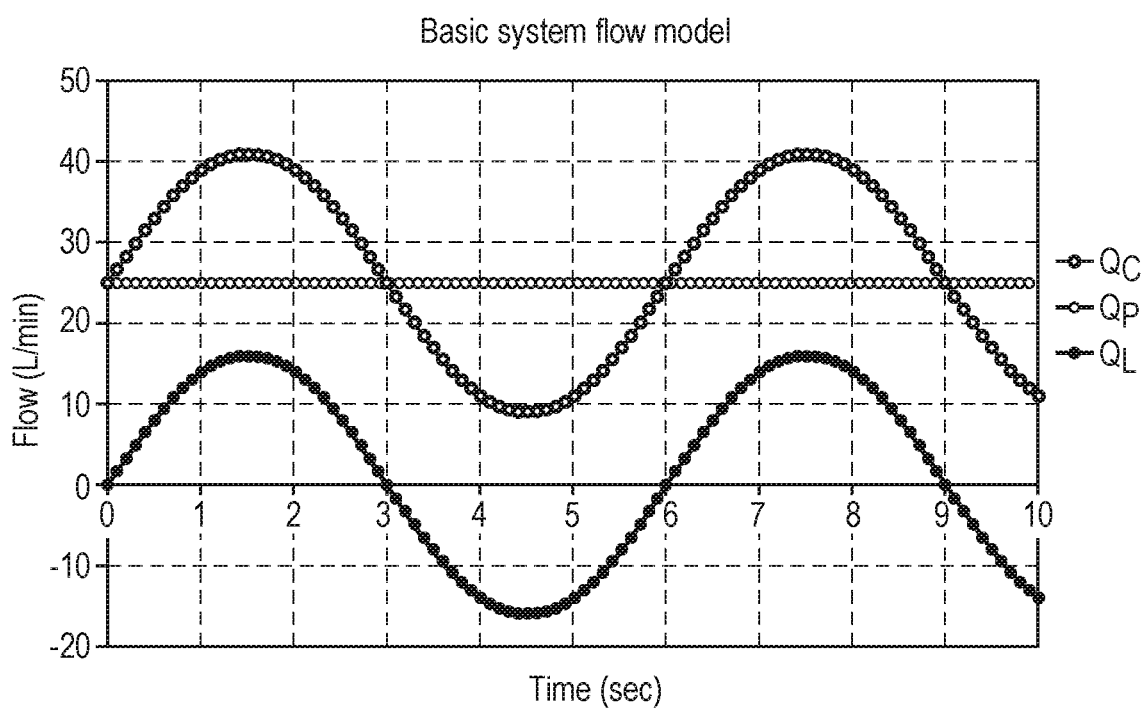
FIG. 15 shows flow signals corresponding to equation (7) described in the specification in accordance with an embodiment of the present patent application.

If patient flow ($Q_P$) is sinusoidal and leak flow ($Q_L$) is constant, a total circuit flow ($Q_C$) signal looks like that shown in FIG. 15. FIG. 15 shows a graphical representation of flow signals corresponding to the equation (7). The flow data is shown on the left hand side Y-axis and the time is shown on X-axis of the graph in FIG. 15. The time is measured in seconds. The flow data is measured in Liters/minute (L/min).

It can be seen in FIG. 15 that integration of a segment of the circuit flow signal, $Q_C$, which is not equal to one or more full cycles, provides different values depending on where the integration starts. The important observation here is that the starting point of integration of the total flow signal to obtain a volume is critical in pursuit of obtaining an accurate volume calculation.

The goal with a perfect algorithm is to turn on humidification so that humidified gas is present at the patient just when he starts to inhale, then ceases just at the end of inhalation phase. The major difficulty is that the patient circuit volume resides between the patient and the humidification source. How to predict when to turn on the humidification before the patient starts breathing is to be determined. In order to effect this, three key assumptions were made 1) the breathing pattern and breath cycle periods remain fairly constant over time; 2) the humidified gas must travel through the patient circuit such that the boundary between a humidified gas portion and a dry gas portion substantially remain separated as they travel down the tube; and 3) the patient circuit volume is known a priori.

Figure 16:
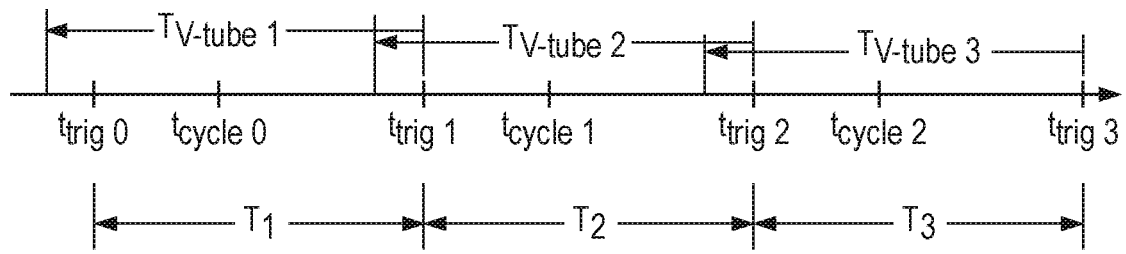
FIG. 16 shows timing diagram for illustrating the timing method for on-demand delivery, wherein the top colored bands indicate the span over which the circuit flow is integrated to pass the patient circuit tube volume and the bottom colored bands show the duration of one full breath cycle each, in accordance with an embodiment of the present patent application.

With these 3 assumptions in place, it is possible to integrate the patient circuit flow until the volume of the patient circuit is reached. At this point, it is known how long it took for that volume to pass through the circuit. This could be used delay to initiate humidification before the next inspiration by the patient. Of course, it is important not only to integrate the flow, but also to know exactly when to start the integration. To address this latter point, FIG. 16 was used. FIG. 16 shows a timing diagram for illustrating the timing method for on-demand delivery. The top colored bands in FIG. 16 indicate the span over which the circuit flow is integrated to pass the patient circuit tube volume. The bottom colored bands in FIG. 16 show the duration of one full breath cycle each.

The span defined as $T_{V_{tube-1}}$ in FIG. 16. The integration for identifying the duration of time for flow to pass through the patient circuit is to be started so that the time period ends exactly at the start of inspiration, $t_{trig-1}$. Although a priori how long this duration is not actually known, how long the duration of the last period can be calculated if the history of flow values is retained for some time, then integrated backwards from $t_{trig-1}$ until $V_{tube}$. This time, $T_{V_{tube-1}}$, is then used to predict when to start the next on-demand cycle of the humidifier for either $t_{trig-2}$ or $t_{trig-3}$, depending on the duration of $T_{V_{tube-1}}$ (if $T_{V_{tube-1}}$ exceeds the duration of the next breath cycle, $T_2$, it may be necessary to start the on-demand cycle for the following breath cycle, $T_3$).

It is assumed that historical values for circuit flow at each time step have been stored, and that those flow values are technically counted backwards in time. The expression for calculating the duration over which flow encompasses the tube volume is shown in equation (8) below.

$$V_{sum} = \sum_{i=0}^{k} Q_{C_i} \quad \text{Equation (8)}$$

where $V_{sum}$=tube volume;
$Q_{C_i}$ is the stored flow value at count i;
i=0 is the count associated with the flow at $t_{trig}$; and
k is the backward count from $t_{trig}$ until $V_{sum} \geq V_{tube}$.

When the summation in equation (8) is finished, the value of count k corresponds to the delay that would be required to start delivering humidity for that breath so that it would reach the patient at the next breath or breaths once the necessary volume has passed through the tube.

One other point that needs to be made regarding circuit volume delay, $T_{V_{tube}}$, and the delay counts, k, is that it is expressly incorrect to interchange values of time and counts. However, because counts are derived from a constant clock frequency used in the ventilator, each count spans substantially the same duration, thus allowing them to be interchangeable.

The delay associated with the patient circuit tubing is now known. Humidified gas during the inspiratory phase can then be delivered. However, the volume delivery flow pattern into the patient circuit used to load the inhaled volume will not correspond with the actual volume delivered during the inspiratory phase unless the patient happens to start inspiration at exactly the same time that the tube starts being loaded from the humidifier. As a result, the tubing loading cannot be simply turned on for the same duration as the inspiratory time. Therefore, the circuit flow volume delivered during the inspiratory phase is to be measured so as to deliver that specific volume into the tube. To measure this volume, equation (9) is used.

$$V_{insp} = \sum_{i=0}^{n} Q_{C_i} \quad \text{Equation (9)}$$

where $V_{insp}$=flow volume delivered during the inspiratory phase;
$Q_{C_i}$=instantaneous (non-stored) flow value at count i;
i=0=count associated with the flow at $t_{trig}$; and
n=count at the following $t_{cycle}$.

The delivery equation then written as equation (10) below:

$$V_{sum2} = \sum_{i=0}^{m} Q_{C_i}, \quad \text{Equation (10)}$$

where $V_{sum2}$=instantaneous value of integrated flow;
$Q_{C_i}$=instantaneous (non-stored) flow value at count i;
i=0=count associated with the flow at $t_{trig}$; and
m=count at which $V_{sum2} \geq V_{insp}$.

Both equations (9) and (10) appear to be identical, but equation (9) is used only to calculate the volume of gas consumed by the patient ($V_{insp}$) and equation (10) is used to set the delivery of gas volume into the tube (done when $V_{sum2} \geq V_{insp}$) starting at k steps (i.e., where k is obtained from equation (8)] prior to the next value of $t_{trig}$.

Invariably, there will be some differences in both timing of k as well as calculation of inspiratory volume on a breath-to-breath basis. If the algorithm above were implemented as described, the system could end up chasing after small unimportant perturbations in these parameters. To avoid this, a low-pass filter should be applied to both the k value as well as $V_{insp}$. The parameters of these filters are worked out empirically by one skilled in the art. In some embodiments, other averaging/smoothing procedures may be applied as would be appreciated by one skilled in the art.

A key assumption necessary for this algorithm to work is that the humidified gas moves as a bolus down the patient circuit. It has been found empirically that bolus flow is in fact a good assumption and can be assumed in the applications presented here.

In summary then, when implementing equation (11), the water is turned on starting at $T_{V_{tube}} = k + k_{shift}$, but not start counting delivery of the tidal volume described in equation (10) until $k_{shift}$ is passed.

Because the approach for figuring out when to preload the patient circuit tube is not based on volume, but is concerned only with time, it does not really matter what shape a patient's inspiratory or expiratory pattern takes. It is also apparent that this algorithm is still useful even in the presence of bi-level pressure delivery, which changes the exhalation valve flow. The timing method is not affected by this, except that the system becomes inaccurate more easily if the breath cycle timing changes because a cycle timing change may translate into a change in the normal contribution of leak, which could greatly affect the tube volume duration measurement.

Invariably, the circuit timing will become disordered due to the addition of mask leak or even changes in patient breath rate or pattern. A simple way to address this is to apply a minimum percent error band outside of which the system reverts to fulltime humidification until it can recover. Such a limit should be placed on both calculation of circuit delay time, $T_{V_{tube}}$, and inspiratory volume $V_{insp}$. Such an approach is shown by equations (12) and (13) below.

$$\text{abs}\left(\frac{T_{V_{tube}} - T_{V_{tube-i}}}{T_{V_{tube}}}\right) > \eta, \quad \text{Equation (12)}$$

$$\text{abs}\left(\frac{\overline{V}_{insp} - V_{insp_i}}{\overline{V}_{insp}}\right) > \eta \qquad \text{Equation (13)}$$

where η is the fractional difference beyond which the system would reset;

abs=absolute value;

$T_{V_{tube}}$=period over which the tube volume is delivered by the ventilator;

i=index of current or past breath cycle;

$V_{inspi}$=inspired volume in breath i; and $T_{V_{tubei}}$=period over which the tube volume is delivered during breath i.

A second approach for the basic algorithm was conceived. This approach requires no timing, but only uses volume measurements that are already making except for the addition of one volume measurement. This method also obviates the need to record and use historical data. FIGS. 17-22 are used to explain this approach. The first is just a realistic record of a set of patient flow and pressure signals, which can be used because the robustness of the algorithm derived above, as well as the new one here obviates the need to have a simple harmonic breathing signal that was used before.

Figure 17:
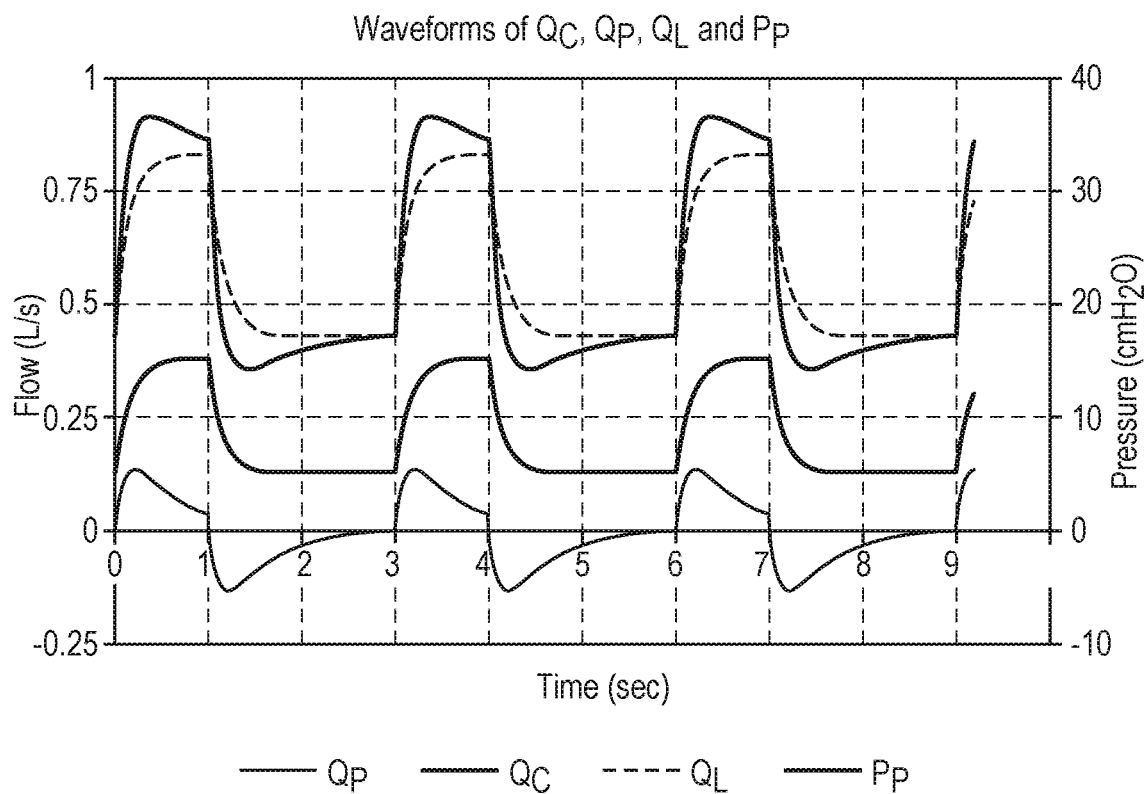
FIG. 17 shows an exemplary graphical representation of patient flow and pressure signals in accordance with an embodiment of the present patent application.

FIG. 17 shows typical patient flow and pressure signals. The top most solid curve is total circuit flow, $Q_c$, the dashed curve from the top is leak flow, $Q_l$, the second solid curve from the top is actual patient flow, $Q_p$, and the third solid curve from the top is delivered pressure, $P_p$ (corresponds to the ordinate on the right). The pressure data is shown on the right hand side Y-axis of the graph in FIG. 17, while the flow data is shown on the left hand side Y-axis of the graph in FIG. 17. The pressure data is measured in centimeters of $H_2O$ (cm $H_2O$). The flow data is measured in Liters/minute (L/min). The time is shown on X-axis of the graph in FIG. 17. The time is measured in seconds.

As was described above, it is necessary to integrate the total flow signal, $Q_c$, to get the value of $V_{insp}$, the total inspired flow. This is shown as the colored region in FIG. 18. The expression for evaluating $V_{insp}$ is given in equation (9) above.

Figure 18:
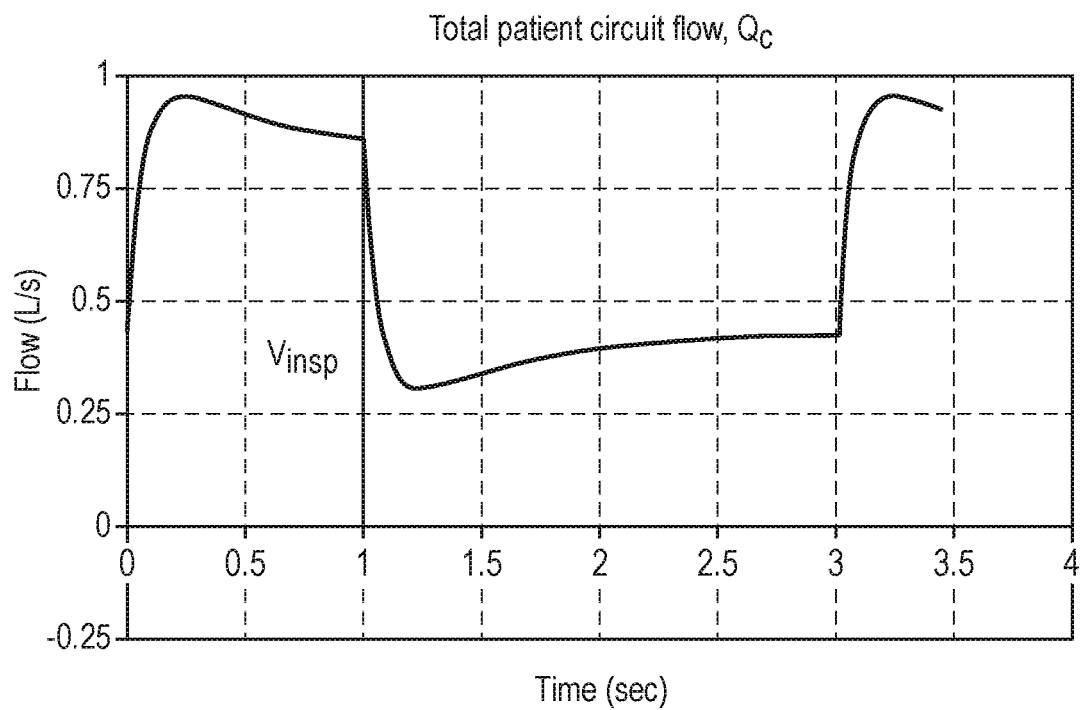
FIG. 18 shows an exemplary graphical representation of total patient circuit flow, where a location and quantification of $V_{insp}$ within breath cycle is shown, in accordance with an embodiment of the present patent application.

FIG. 18 shows location and quantification of $V_{insp}$ within the breath cycle. FIG. 18 shows total patient circuit flow signal, $Q_c$. The flow data is shown on the left hand side Y-axis of the graph in FIG. 18. The flow data is measured in Liters/minute (L/min). The time is shown on X-axis of the graph in FIG. 18. The time is measured in seconds. The total inspiratory volume by integrating from beginning to end of an inspiratory phase, $V_{insp}$ is the shaded area in FIG. 18.

The next step is to integrate the total flow to obtain the volume delivered during the entire breath cycle. For now, what happens if exhalation flow exceeds leak flow is ignored, resulting in retrograde flow in the patient circuit back toward the ventilator. The volume of total flow over the breath cycle is highlighted in yellow in FIG. 19. FIG. 19 shows location and quantification of the total breath volume, $V_{tot}$, for one breath cycle. FIG. 19 shows total patient circuit flow signal, $Q_c$. The flow data is shown on the left hand side Y-axis of the graph in FIG. 19. The flow data is measured in Liters/minute (L/min). The time is shown on X-axis of the graph in FIG. 19. The time is measured in seconds. The total volume over one breath phase, $V_{tot}$ is the shaded area in FIG. 19.

The integral is shown in equation (14) below $$V_{tot} = \sum_{i=0}^{N} Q_{C_i} \qquad \text{Equation (14)}$$

where $V_{tot}$=total volume delivered by the vent during a breath;

$Q_c$=total patient circuit flow;

i=0=count associated with the flow at $t_{trig}$; and

N=count at the end of the cycle, or that corresponding to $t_{trig}$.

The volume of $V_{tube}$ is subtracted from the total volume, $V_{tot}$. When this volume is reached from the beginning of the next or any subsequent breath cycle, the turn_on time is reached as shown in FIG. 20. FIG. 20 shows volume encompassed by the difference between tube volume, $V_{tube}$, and total volume, $V_{tot}$. The tube volume described above, $V_{tube}$ is shown in FIG. 20. In some embodiments, $V_{tube}$ is input by the user. In some embodiments, $V_{tube}$ is calculated by the ventilator. FIG. 20 shows total patient circuit flow signal, $Q_c$. The flow data is shown on the left hand side Y-axis of the graph in FIG. 20. The flow data is measured in Liters/minute (L/min). The time is shown on X-axis of the graph in FIG. 20. The time is measured in seconds.

This may not be intuitive at first glance, so it is noted that in whatever algorithm is used, it is always necessary to use historical information in order to predict when to turn on the oxygen or water. In the previous algorithm, historical flow information was stored and this flow information was integrated backwards from the start of inspiration to find the time at which $V_{tube}$ passed. In this case, instead of storing old flow values and integrating, the total volume essentially provides the only historical information needed, which eliminates the need to store more than one element of historical data of any kind. In other words, the value of $V_{tot}$ is the historical information.

It is only necessary to see then that the tube volume subtracted from total volume sets the on_time because the algorithm requires going backwards in time from $t_{trig}$ until volume is equal to $V_{tube}$, as done above. However, by subtracting $V_{tube}$ from $V_{tot}$, the same point in time is exactly obtained. Therefore, delivery of oxygen or water is started at turn_on, then it is shut off after delivery of $V_{insp}$ as described above. This is shown in FIG. 21.

FIG. 21 shows delivery of the inspiratory volume, $V_{insp}$, starting at turn_on and stopping at turn_off. FIG. 21 shows the total patient circuit flow signal, $Q_c$. The flow data is shown on the left hand side Y-axis of the graph in FIG. 21. The flow data is measured in Liters/minute (L/min). The time is shown on X-axis of the graph in FIG. 21. The time is measured in seconds.

There are other circumstances in which the algorithm described here will need to be modified slightly in order to make the necessary accommodations. These circumstances are described below, but for now it is pointed out that in order to provide maximum comfort and safety to the patient, a margin for turning on the inspired volume is provided. No adjustments on the turn_off end are made because the final portion of the inspiratory phase only delivers into the anatomic deadspace.

FIG. 22 shows adding a margin to turn_on. FIG. 22 shows total patient circuit flow signal, $Q_c$. The flow data is shown on the left hand side Y-axis of the graph in FIG. 22. The flow data is measured in Liters/minute (L/min). The time is shown on X-axis of the graph in FIG. 22. The time is measured in seconds.

It should be noted at this point that in cases where the tidal volume is small and the breath rate is high, such as with neonates, it could easily be the case that the value of $V_{tot}-V_{tube}$ is negative. This presents a problem because a negative value can in no way create a sufficient delay for compensation of the patient circuit tubing, $V_{tube}$.

To circumvent this problem, it is necessary to assure that this value exceeds 0. To do this requires integration of the total flow over multiple breaths until the difference, $V_{tot}-V_{tube}$ becomes positive at the end of a breath cycle. Although not necessary, it is recommended that a new integration start with each new breath cycle, such that there could be many integrations proceeding in parallel, all with the same goal of reaching a positive value of the volume difference at the end of a breath cycle. Therefore, the algorithm for calculating $V_{tot}$ is shown in equation (15) below.

$$V_{tot} = \sum_{i=0}^{mN} Q_{C_i} \qquad \text{Equation (15)}$$

where $V_{tot}$=total volume delivered by the vent for a given breath;
$Q_c$=total patient circuit flow;
i=time step that starts at the beginning of a breath cycle;
N=number of time steps in a full breath; and
m=number of full breaths, and its value is reached when $V_{tot}-V_{tube}>0$.

It is finally noted here that the value of the tube volume, $V_{tube}$, includes various things depending on the circuit configuration and the entity being controlled.

Humidification is a very simple case because the only volume for which compensation is necessary is that between the humidifier outlet and the patient. It will be assumed that this is simply the patient circuit tubing. The equation (16) shows the tube volume equals the patient circuit tubing volume.

$$V_{tube}=V_{circuit} \qquad \text{Equation (16)}$$

where $V_{tube}$=tube volume; and
$V_{circuit}$=patient circuit tubing volume.

For oxygen mixing, the value of the tube volume $V_{tube}$ is a bit more complex because it encompasses a number of different things that may or may not be present in the circuit. These include a) patient circuit tubing, $V_{circuit}$, (i.e., always present); b) humidifier bowl, $V_{bowl}$, (i.e., optional but likely present) 3) humidifier connection tube, $V_{connect}$, (i.e., always with humidifier ~175 cc); 4) Oxygen Blending Module Volume, $V_{OBM}$, (i.e., always present—XX cc) and 5) the ventilator internal flow path volume, $V_{vent}$. If all components listed above are present, the tube volume $V_{tube}$ is shown by equation (17) below.

$$V_{tube}=V_{circuit}+V_{bowl}+V_{connect}+V_{OBM}+V_{vent} \qquad \text{Equation (17)}$$

where $V_{bowl}$=humidifier bowl volume;
$V_{OBM}$=oxygen blending module volume;
$V_{connect}$=humidifier connection tube volume;
$V_{circuit}$=patient circuit tubing volume; and
$V_{vent}$=ventilator internal flow path volume.

Another issue of concern regarding the volumes measured as described above, is the quantification of air volume delivered into the compliance due to its compressibility. For measured parameters, volume is known exactly, so it is not necessary to compensate for this. However, the tubing volume that must be entered by the user, $V_{tube}$, is a constant value that will be affected by compliance.

It is known that patient circuit tubing, as well as the additional hard plumbing within the ventilator, can be assumed to be non-compliant, but it is also known that the compliance due to gas compressibility is not. The compliance of air in some volume is expressed as shown in equation (18) below.

$$C = \frac{V}{P_{tot}} \qquad \text{Equation (18)}$$

where C=compressible gas compliance,
V=volume of interest, in this case, $V_{tube}$, and
$P_{tot}$=absolute pressure in that volume, which shown in equation (19) below.

$$P_{tot}=P_{vent}+P_{atm} \qquad \text{Equation (19)}$$

where $P_{vent}$=gage ventilatory pressure;
$P_{tot}$=absolute pressure in the volume of interest, in this case,
$V_{tube}$;
$P_{atm}$=local atmospheric pressure.

If a case where $P_{vent}$ is 20 cmH$_2$O and the total pressure is 1000 cmH$_2$O, for a 6 feet, 22 mm patient circuit, the volume is approximately 700 cc. Using these in equation (17), the compressible gas compliance is 0.70 cc/cmH$_2$O. Thus, if the circuit from 0 to 20 cmH$_2$O was pressurized, there will be an additional volume accumulated due to gas compression compliance of about 14 cc. This volume represents only 2% of the total volume of the circuit.

However, a much worse case would be if a larger tube volume and a lower atmospheric pressure are considered. A larger tube volume would be present when using a humidifier (1320 cc [695+450+175]) and a very low pressure would exist at 10,000 ft (~700 cmH$_2$O). With these, the compliance becomes 1.89 cc/cmH$_2$O. A pressure change of 20 cmH$_2$O then corresponds to a compliance volume change of 38 cc, which is just under 3% of the total volume. If the pressure change is 40 cmH$_2$O instead of 20 cmH$_2$O, that percentage doubles to just over 5.5% of the total volume. It can be said that this last number is probably the worst possible case for compliance. To make this clearer, sample values were taken and put in the table shown in FIG. 23. The table in FIG. 23 shows samples of tubing gas compression compliance results. The final column is the percent that compliance volume is relative to the total volume.

It can further be considered what would happen if there was no compensation for compression volume. In an absolute worst case, the error is just shy of 6% of the total volume. This is not insignificant in say a 22 mm tube that has a volume of 695 cc, in which case the error is about 40 cc. Thus, it is recommended that compensation for compliance occur.

Perfectly optimized delivery of compliance compensation gas is quite complex because the delivery of the inspiratory volume into the circuit can occur when the circuit is at either inspiratory or expiratory pressures or during both. Thus, the compliance volume may vary even while the inspiratory volume is being delivered. To avoid these complexities, it is erred on the side of accommodating the patient by adding margin volume that corresponds to the worst case for the given operating conditions. The margin volume is calculated as shown in equation (20) below.

$$V_{margin} = CP_{vent_{peak}} = \frac{V_{tube}}{P_{atm}} P_{vent_{peak}}, \quad \text{Equation (20)}$$

where $P_{vent_{peak}}$=peak gage pressure used during ventilation;
$P_{atm}$=local atmospheric pressure;
C=compressible gas compliance; and
$V_{margin}$=margin volume;

The margin volume, $V_{margin}$, would then be applied as indicated in FIG. 22. To implement it, it is first necessary to find out how far to shift the value of turn_on. To do this, the margin volume, $V_{margin}$ is simply added to $V_{tube}$ when calculating $V_{tot}$-$V_{tube}$. The volume for turn_on is calculated as shown in equation (21) below.

$$V_{turn\_on} = V_{tot} - (V_{tube} + V_{margin}) \quad \text{Equation (21)}$$

where $V_{turn\_on}$=turn_on volume; and
$V_{tot}$=total breath volume.

Consequently, the volume to be delivered to cover the inspiratory volume, $V_{insp}$ is shown in equation (22) below $$V_{turn\_off} = V_{insp} + V_{margin} \quad \text{Equation (22)}$$

where $V_{turn\_off}$=turn_off volume; and
$V_{insp}$=inspiratory volume.

For a normal adult, anatomic deadspace comprises about 150 cubic centimeter(cc), or just under ⅓ of any breath in tidal breathing. This means that the last third or so of gas provides no ventilatory benefit to the patient, but is simply a space filler. For humidification, it would be important to keep deadspace gas humidified so as not to allow the upper airways to dry out.

However, for oxygen delivery, any gas in the anatomic deadspace would be wasted. Thus, the algorithm could include a method to not deliver gas into the anatomic deadspace. To do this, the delivery of oxygen is simply stopped some fraction of the inspired volume short. This is written as shown in equation (23) below.

$$V_{turn\_off} = (1 - \beta_{DS})(V_{insp} + V_{margin}) \quad \text{Equation (23)}$$

where $\beta_{DS}$=fraction of patient tidal volume that represents anatomic deadspace.

Whenever patient circuit flow is negative, it is necessary to remain cognizant of the fact that for the next inhalation, the patient circuit must contain gas with the following characteristics 1) it must be an uninterrupted slug residing in the patient circuit tube; 2) the gas entire gas slug must be enriched to the same level; 3) the delivered gas slug must have a volume equal to $V_{insp}$; 4) the algorithm cannot account for re-breathing if the ventilation is insufficient to drive off excess $CO_2$; and 5) as long as leak is >0, on average, the volume of negative flow, $V_{neg}$ must be less than $V_{insp}$.

The problem is that this slug of delivered enriched gas could start at any time, a fact that is complicated only when exhaled flow exceeds leak flow (i.e., retrograde flow). If there is retrograde flow, the correct response in how to deal with it is dictated by the type of case present. In all of these cases, it is assumed that retrograde flow only occurs for one period of duration during delivery of a single tidal volume. The cases for consideration include 1) no retrograde flow; 2) enrichment starts after retrograde flow has ceased; 3) enrichment is started, retrograde flow begins after this point, but retrograde volume does not exceed $V_{UV}$, which is the volume upstream from the enrichment point; and 4) enrichment is started, retrograde flow begins after this point, retrograde flow exceeds $V_{UV}$.

The case in which there is no retrograde flow is considered first. This is the same case as that without retrograde flow. Enriched flow is simply delivered through the volume, $V_{insp}$.

The case in which enrichment starts post retrograde flow is considered next. That is, the enrichment starts after retrograde flow has ceased. This is the same case as that without retrograde flow. Enriched flow is simply delivered through the volume, $V_{insp}$.

The case in which the enrichment is started, retrograde flow begins after this point, but the retrograde volume does not exceed $V_{UV}$, which is the volume upstream from the enrichment point (i.e., $V_{neg} \leq V_{UV}$) is considered next. In this case, the following rules apply: 1) start the volume delivery integration at the appropriate point; 2) stop the volume delivery integration as soon as flow becomes negative and retain the integrator value; 3) start integrating the negative flow, $V_{neg}(t)$; and 4) once flow changes direction, store the value of negative flow volume, $V_{neg}$, then start to unwind the negative flow integrator. Once the negative flow integrator reverts to 0, a) restart the volume delivery integration from the point at which it was previously stopped; and b) restart enrichment delivery again through the end of $V_{insp}$.

The case in which the enrichment is started, retrograde flow begins after this point, retrograde flow exceeds $V_{UV}$ ($V_{neg} > V_{UV}$) is considered next.

In this case, the following rules apply. If $V_{insp\_start} \geq V_{neg}$, 1) start volume delivery at the appropriate point; 2) measure the volume of positive gas flow from the time at which $V_{insp}$ is started, until the beginning of retrograde flow. This will be designated $V_{insp\_start}$; 3) when the quantity of volume equal to ($V_{insp\_start} - V_{neg}$) has been delivered into the patient circuit, stop delivery of enrichment and stop the volume delivery integration but retain its value; 4) once flow becomes negative start the negative flow integrator; and 5) once flow changes direction, restart enrichment and restart the volume delivery integrator. If $V_{insp\_start} < V_{neg}$, 1) don't start gas delivery until positive flow recovers; and 2) then use the case in which there is no retrograde flow above.

In the following sections of the present patent application, a model of the savings from a passive flow circuit is presented. The savings for a passive flow circuit is expected to be around 50% with a passive patient circuit, and could be 100% with an active flow circuit.

As part of the development of true on-demand humidification delivery, it is important to be able to predict the savings in water incumbent in such a design. Below the analysis is outlined and a prediction of the quantity of water that can be saved in perfect on-demand delivery is also provided.

The prediction for water savings is based on a simple model that describes water added to gas as it travels through the humidifier then down the patient circuit. This model is based on the idea that flow from exhalation valve EV is only a function of circuit pressure and is represented by a model for inspiration and one for expiration as shown in FIG. 24.

In FIG. 24, the left figure shows the gas volume movement during the inspiratory phase, while that on the right (in FIG. 24) shows the gas volume movement during the expiratory phase.

Referring to the inspiratory and expiratory phase models shown in FIG. 24, summing according to the direction of the arrows to the connection point in either model in FIG. 24 results in equations (24) and (24) below.

According to the equation (24), volume that passes through the humidifier during the inspiratory phase, $V_{insp}$ is equal to sum of the tidal volume, $V_t$ and the total volume that leaves the exhalation valve during the inspiratory phase, $V_{exh_i}$.

According to the equation (25), volume that passes through the humidifier during the expiratory phase, $V_{exp}$ is equal to difference between of the total volume that leaves the exhalation valve during the expiratory phase, $V_{exh_e}$ and the tidal volume, $V_t$.

$$V_{insp} = V_t + V_{exh_i} \quad \text{Equation (24)}$$

$$V_{exp} = V_{exh_e} - V_t, \quad \text{Equation (25)}$$

where $V_{insp}$=volume that passes through the humidifier during the inspiratory phase;

$V_{exp}$=volume that passes through the humidifier during the expiratory phase;

$V_{exh_i}$=total volume that leaves the exhalation valve during the inspiratory phase;

$V_t$=tidal volume; and $V_{exh_e}$ total volume that leaves the exhalation valve during the expiratory phase.

A couple of assumptions (referring to FIG. 24 and the equations (24) and (25) above) that are important in this analysis are noted here. For a given circuit pressure, there will be a specific exhalation flow regardless of what the patient is doing. In this approach, fluctuations in pressure are ignored and assumed that those pressures are constant during the inspiratory and expiratory phases, although those pressures will not necessarily be the same (Continuous Positive Airway Pressure (CPAP) vs Bilevel Positive Airway Pressure (BiPAP)).

Another key assumption in this analysis is that the timing and consistency of pressure are the same through both the inspiratory and expiratory phases such that the volume matching that is inherent in the models in FIG. 24 can be performed validly.

Lastly, it is assumed that because the volumes that pass through the humidifier are being compared, any volume that goes through the humidifier receives the same fraction of water, allowing one to use only volume to estimate water savings. It is likely true that higher gas flows through a humidifier may well pick up less water due to reduced residence time. Thus, it would be extremely difficult to assess the effect in all cases, so it is assumed the water content is proportional to volume. Using this, one can employ the model above to write the water savings as a percentage by relating the ratio of the volumes of water per breath with no water delivered during the expiratory phase to the water per breath with water delivered during the entire breath.

The water savings are then calculated by assuming perfect operation of an on-demand algorithm such that water is delivered only during the inspiratory phase, and none during the expiratory phase. The savings is then equal to the ratio of expiratory water loss to total water loss in normal operation, which can be written as shown in equation (26) below. The sum of the volume that passes through the humidifier during the inspiratory phase, $V_{insp}$ and the volume that passes through the humidifier during the expiratory phase, $V_{exp}$ equals to the total water loss in normal operation (i.e., denominator in the equation (26) below).

$$\% \text{ Savings} = \frac{V_{exp}}{V_{insp} + V_{exp}} \quad \text{Equation (26)}$$

where $V_{insp}$=volume that passes through the humidifier during the inspiratory phase; and $V_{exp}$=volume that passes through the humidifier during the expiratory phase.

Figure 25:
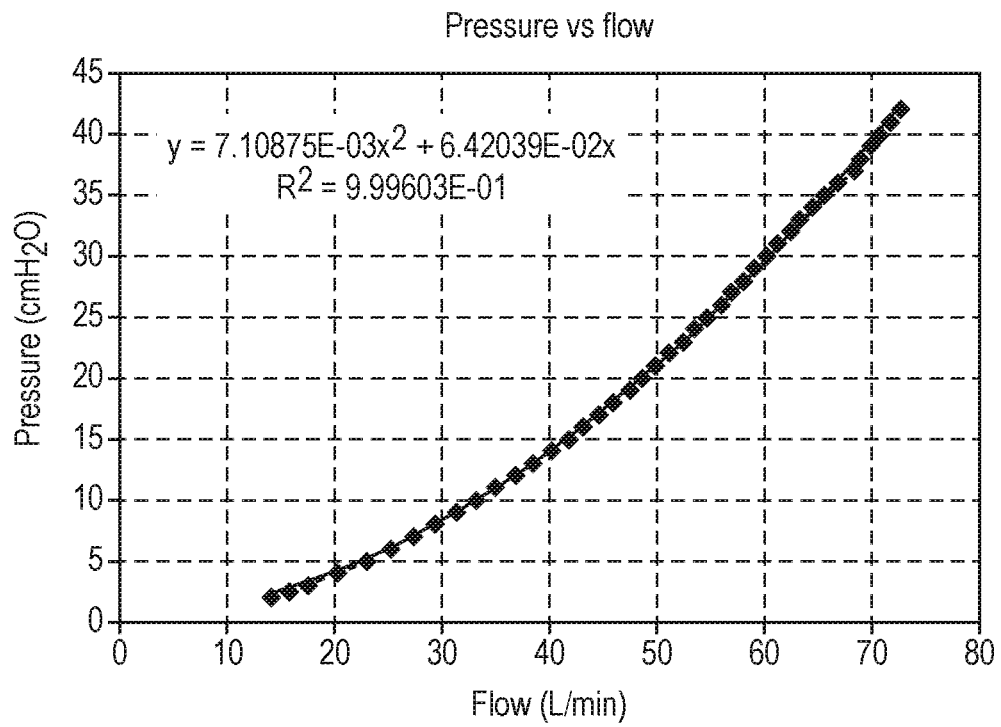
FIG. 25 shows an exemplary graphical representation of pressure versus flow information in accordance with an embodiment of the present patent application.

Regarding the leak valve flow rate, an exhaust valve was used to predict flow rate as a function of pressure. A graph and curve-fit of this relationship is presented in FIG. 25. That is, FIG. 25 shows pressure vs flow and the curve-fit function. The pressure data is shown on the left hand side Y-axis of the graph in FIG. 25. The pressure data is measured in centimeters of $H_2O$ (cm $H_2O$). The flow data is shown on X-axis of the graph in FIG. 25. The flow/volume data is measured in Liters/minute (L/min).

This curve in FIG. 25 follows the shape of a $2^{nd}$-order polynomial, so that is why the curve-fit given in FIG. 25 was chosen. Moreover, because of the fact that the original data set does not possess values below 12 or so L/min, this curve-fit was forced through 0 so that the flow rates that were calculated were limited to this requirement.

The goal of using this curve-fit in this analysis is to allow one to use pressure, which is known, to calculate leak flow, which is unknown. However, since the curve-fit is $2^{nd}$-order, the quadratic formula was used to calculate flow since the general expression for a $2^{nd}$-order polynomial has 2 roots in the independent variable, flow. This is shown in equation (27) below. In the equation (27), the offset pressure, $P_{offset}$ is measured in $cmH_2O$; the laminar resistance, $R_L$ is measured in $cmH_2O/L/min$; and the turbulent resistance, $R_T$ is measured in $cmH_2O/L^2/min^2$.

$$\Delta P = R_T Q^2 + R_L Q + P_{offset}, \quad \text{Equation (27)}$$

where $R_T$=turbulent resistance;

$\Delta P$=change in pressure;

Q=flow;

$R_L$=laminar resistance; and $P_{offset}$=offset pressure.

To solve for the flow, Q, all the terms on the right side of the equation (27) are isolated to obtain the following equation (28). Each of the terms in the equation (28) are described in the equation (27) above.

$$0 = R_T Q^2 + R_L Q + (P_{offset} - \Delta P) \quad \text{Equation (28)}$$

The quadratic formula starts with a polynomial written in the form as shown in equation (29). In the equation (29), Q is the flow, and a, b and c are the coefficients.

$$0 = aQ^2 + bQ + c \quad \text{Equation (29)}$$

In this model, the curve-fit was forced through 0, so the term, $P_{offset}$, has a value of 0. Using the curve-fit from FIG. 25 in conjunction with the coefficients in the equations (28) and (29), the coefficients can be in the form as shown by equations (30)-(32) below. Each of the terms in the equations (30)-(32) are described in the equations (27) and (29) above.

$$a = R_T = 7.10875 \times 10^{-3} \quad \text{Equation (30)}$$

$$b = R_L = 6.42039 \times 10^{-2} \quad \text{Equation (31)}$$

$$c = -\Delta P \quad \text{Equation (32)}$$

The numerical values provided in equations 30 and 31 were measured for the exhalation port of one of our sleep masks. The quadratic formula can then be written as shown in equation (33) below.

$$Q_{1,2} = \frac{-b \pm \sqrt{b^2 - 4ac}}{2a} \qquad \text{Equation (33)}$$

It is also noted from experience that the valid term for the solution for the flow is the positive term in the numerator, so the equation (33) can be rewritten as equation (34) shown below. Each of the terms in the equations (33)-(34) are described in the equations (27) and (29) above.

$$Q = \frac{-b + \sqrt{b^2 - 4ac}}{2a} \qquad \text{Equation (34)}$$

The variables that affect the % water savings include the following a) I:E (inspiratory:expiratory ratio); b) breath rate; c) tidal volume; d) Continuous Positive Airway Pressure (CPAP) level; e) Bilevel Positive Airway Pressure (BiPAP) combinations; and/or f) additional leak such as mask leak, which will be modeled as a constant flow rate. After setting up the model, a series of cases were run where each of the variables listed above are varied over some reasonable range and the effect on % water savings is calculated.

FIGS. 26-32 are the plots of the model looking at each of these variables discussed above. In each, the list of values associated with all of the other variables is provided on each plot. Again, it is noted that the % water saved is the amount of water not needed when using a perfect on-demand algorithm as compared with operating under the same parameters with water added continuously. Also, the span of the ordinate is the same for all plots, and a red marker indicates a point that is associated with baseline conditions.

FIGS. 26-32 show graphical representations of on-demand % water saved when varying different parameters. The % water saved is shown on the left hand side Y-axis of the graphs in FIGS. 26-32. The % water saved data is measured in percentage.

Figure 26:
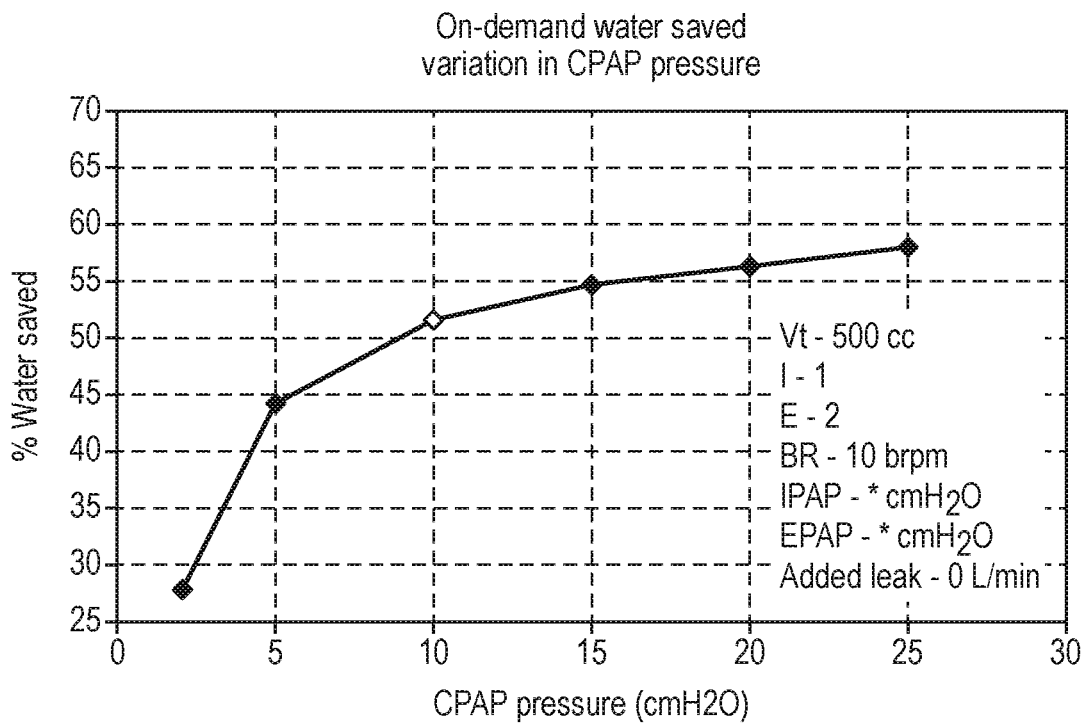
FIG. 26 shows an exemplary graphical representation of percentage of water saved with a variation in Continuous positive airway pressure (CPAP) in accordance with an embodiment of the present patent application.

FIG. 26 shows the % water saved when the Continuous Positive Airway Pressure (CPAP) pressure is varied. The Continuous Positive Airway Pressure (CPAP) pressure is shown on X-axis of the graph in FIG. 26. The Continuous Positive Airway Pressure (CPAP) pressure is measured in centimeters of $H_2O$ (cm $H_2O$).

Figure 27:
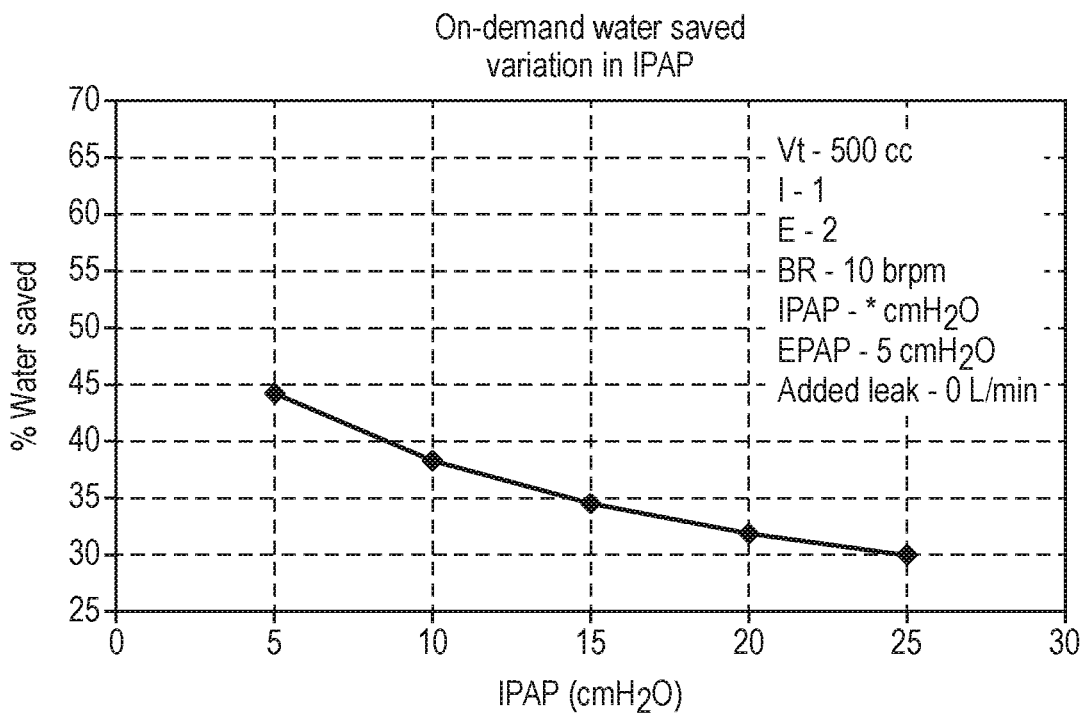
FIG. 27 shows an exemplary graphical representation of percentage of water saved with a variation in Inspiratory positive air pressure (IPAP) in accordance with an embodiment of the present patent application.

FIG. 27 shows the % water saved when the Inspiratory Positive Airway Pressure (IPAP) pressure is varied. The Inspiratory Positive Airway Pressure (IPAP) pressure is shown on X-axis of the graph in FIG. 27. The Inspiratory Positive Airway Pressure (IPAP) pressure is measured in centimeters of $H_2O$ (cm $H_2O$).

Figure 28:
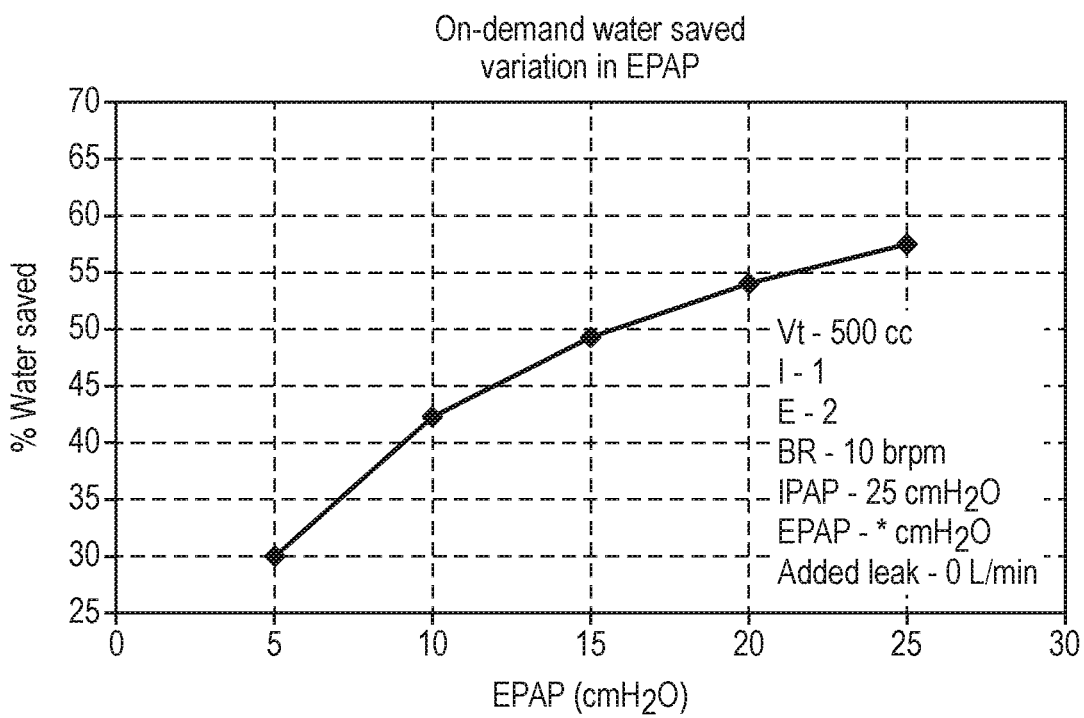
FIG. 28 shows an exemplary graphical representation of percentage of water saved with a variation in Expiratory positive air pressure (EPAP) pressure in accordance with an embodiment of the present patent application.

FIG. 28 shows the % water saved when the Expiratory Positive Airway Pressure (CPAP) pressure is varied. The Expiratory Positive Airway Pressure (CPAP) pressure is shown on X-axis of the graph in FIG. 28. The Expiratory Positive Airway Pressure (CPAP) pressure is measured in centimeters of $H_2O$ (cm $H_2O$).

Figure 29:
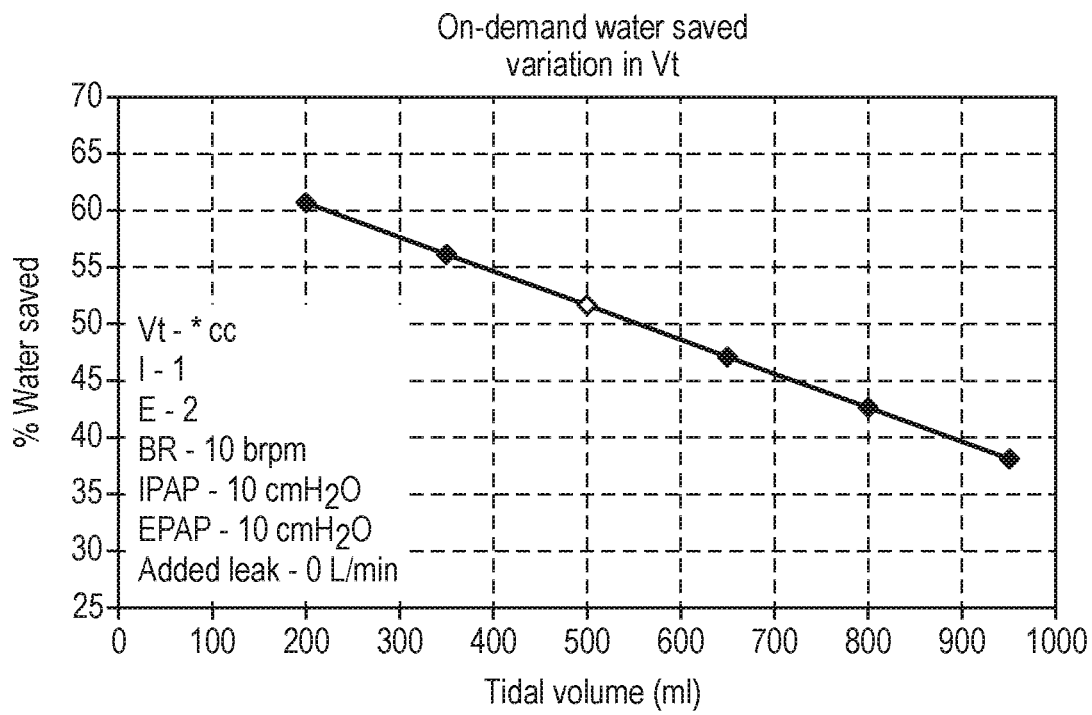
FIG. 29 shows an exemplary graphical representation of percentage of water saved with a variation in tidal volume in accordance with an embodiment of the present patent application.

FIG. 29 shows the % water saved when the tidal volume is varied. The tidal volume is shown on X-axis of the graph in FIG. 29. The tidal volume is measured in milliliters (ml).

Figure 30:
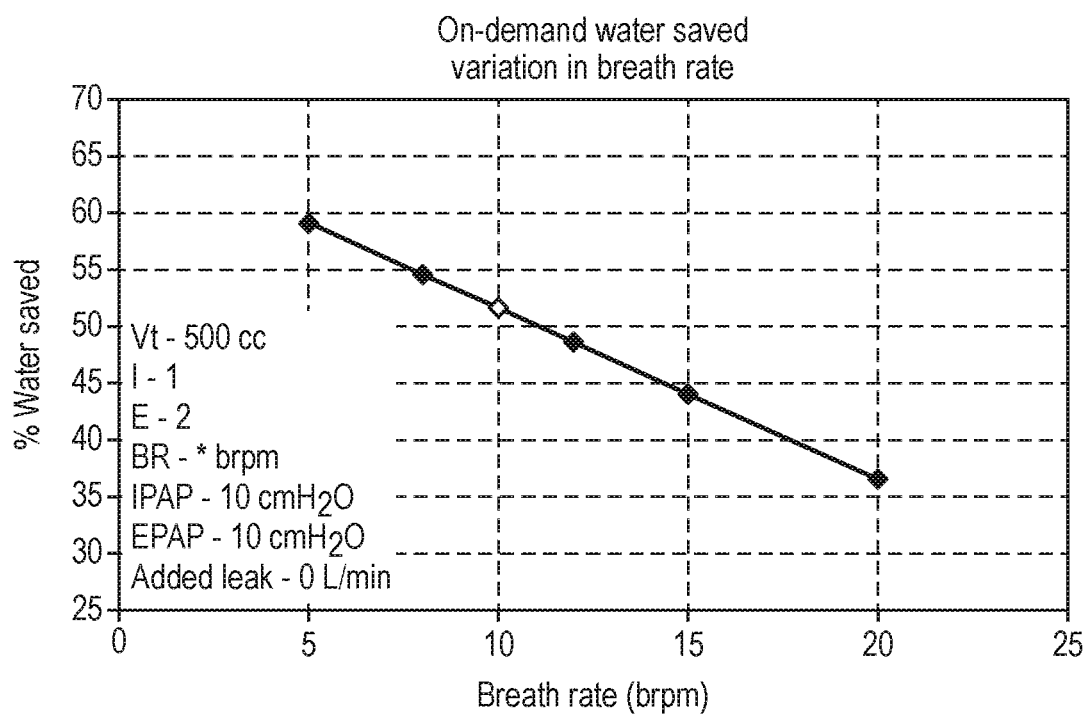
FIG. 30 shows an exemplary graphical representation of percentage of water saved with breath rate in accordance with an embodiment of the present patent application.

FIG. 30 shows % water saved when the breath rate is varied. The breath rate is shown on X-axis of the graph in FIG. 30. The breath rate is measured in breath rate per minute (brpm).

Figure 31:
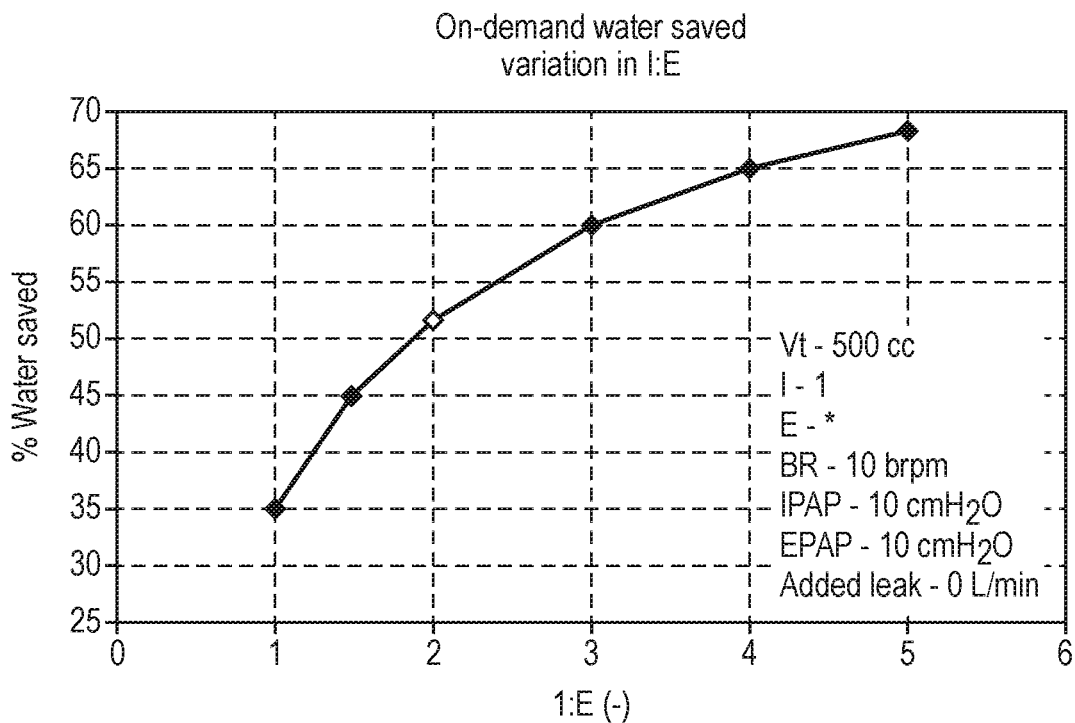
FIG. 31 shows an exemplary graphical representation of percentage of water saved with I:E (inspiratory:expiratory ratio) in accordance with an embodiment of the present patent application.

FIG. 31 shows the % water saved when the I:E (inspiratory:expiratory ratio) is varied. The I:E (inspiratory:expiratory ratio) is shown on X-axis of the graph in FIG. 31.

Figure 32:
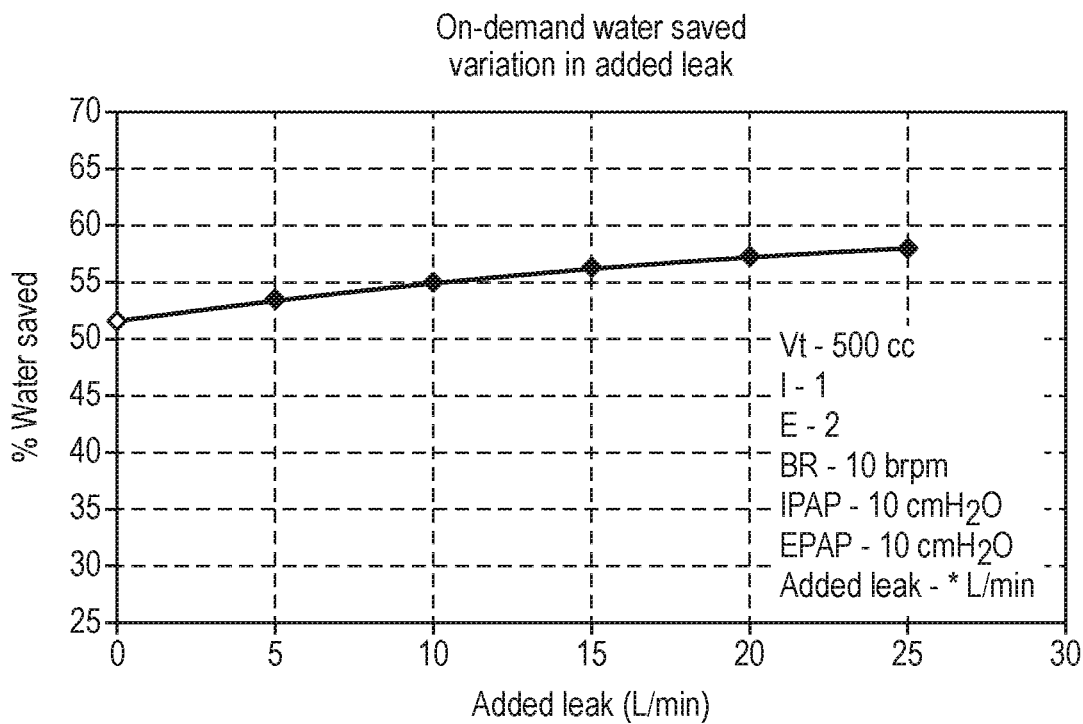
FIG. 32 shows an exemplary graphical representation of percentage of water saved with additional leak in accordance with an embodiment of the present patent application.

FIG. 32 shows % water saved when the additional leak is varied. The additional leak is shown on X-axis of the graph in FIG. 32. The additional leak is measured in liters/minute (L/min).

To make the analysis easier to evaluate, the range of each of these parameters are assembled into the table shown in FIG. 33. The table in FIG. 33 shows summary of % water saved ranges for each of the parameters used in the model. Because the parameter range is listed in order from low to high, and the Upper, Lower and % water saved are listed without indicating order relative to the parameter range, the Curve Slope was added to indicate direction of the water savings.

In the analysis, it was assumed that the ranges used for each parameter are reasonable insofar as they cover a legitimate span of minimum to maximum values. Given that, the total range of savings runs from about 30% to up to 60-70%. It can be further seen that for the ranges chosen, changes in IPAP and additional leak have lower impact on % water saved than other parameters, and that CPAP, EPAP and the I:E ratio have the greatest impact. Again, this conclusion is potentially limited in proportion to the veracity of the parameter ranges chosen in this analysis. Also, note that only one parameter at a time was changed in this analysis, and have not evaluated the effects of combining variable changes.

It must be noted that there are other limitations to the model presented here that would cut into the % savings. These limitations may include the following, for example, any on-demand algorithm is not going to be completely accurate for a number of reasons, such as the mixing of wet gas with dry gas as it goes down the circuit, and the algorithm should err on the side of assuring the correct humidification during the inspiratory phase, which would require operating the "on" phase longer than would occur with precise timing. Such an error most likely represents a small change in the percentages delineated in Table (in FIG. 33) however. These limitations may include the following, for example, because any on-demand algorithm must necessarily predict when to turn on the water assuming that the water delivery mechanism is 6 or so feet away from the patient, such an algorithm can work precisely only when a patient breathes with a constant cadence. If the patient cadence does vary, the algorithm must necessarily err on the side of staying on longer, with the ultimate fallback being that the water should be delivered continuously. For a patient who has a highly variable cadence, it is possible that in the extreme case, the on-demand algorithm may effectively not be used at all, meaning that it is possible that some patients may not be able to take advantage of the water savings.

In some embodiments, water savings in a very accurate on-demand system is on the order of 30%-60-70%, suggesting that a savings of 50% could be targeted. Note that this range was identified only by changing one input at a time, and does not include worse or better cases that might be associated with combining changes in various input values.

In some embodiments, changes in IPAP and additional leak seem to have the lowest impact on water saved while CPAP, EPAP and I:E seem to have the greatest impact.

In some embodiments, the model of perfect algorithmic timing is not really plausible in reality, which means that the range stated is at least going to be a few percentage points lower even if the patient has very consistent breath cadence. In some embodiments, for patients who have poor cadence, it is possible that some patients may require the algorithm to deliver water nearly continuously.

In some embodiments, it is possible that prudence may require that current water chamber sizes must be used even in an on-demand system to cover patients with poor cadence. However, if this is the case, an on-demand still provides other benefits such as, but not limited to, a) longer use of the single fill of a water reservoir for patients with good cadence; and b) less rainout resulting from the drying effect of the "off" condition of the algorithm.

System 100 was conceived in response to complaints by clinicians of the problem regarding excessive waste of oxygen when using the ventilator. System 100 reduces or eliminates supplemental gas waste (oxygen or water vapor) when using a pressure support ventilator with a passive flow circuit. For oxygen, the savings is brought any time that bottled gas is used. For an oxygen concentrator, the algorithm enhances the $FiO_2$ of the gas for the same concentrator flow rate without the algorithm. When used to limit delivery of humidity, the benefits include: a) reduced water usage that can 1] extend water reservoir life of 2] allow the construction of a smaller humidifier; b) reduce rainout in the patient circuit because dry air passes through the tube most of the time; and c) reduces electrical power consumption because only half of the water is being delivered as humidity.

In some embodiments, system 100 includes the algorithm that controls titrating supplemental gas delivery into patient circuit 106 so that it shows up at the patient when the patient begins to inhale and stops showing up when the patient finishes inhaling. In some embodiments, the algorithm is a software algorithm that can be used in the applications described throughout this patent application. For example, this algorithm is in applications such as, but not limited to, 1) reducing CPAP humidifier water usage by using a valve inside the humidifier chamber to allow air either through the humidifier or around the humidifier as directed by the algorithm; 2) reducing oxygen waste in an oxygen blending module of a pressure support ventilator; 3) reducing oxygen waste from bottled oxygen bled into the low-flow inlet port of a pressure support ventilator; and 4) improving oxygen fraction delivery from concentrator oxygen bled into the low-flow inlet port of the pressure support ventilator.

In some embodiments, system 100 is used on any ventilator that possesses an oxygen blending module or low-flow oxygen port. In some embodiments, system 100 is used with any humidifier in conjunction with ventilation operation.

In some embodiments, an external flow measurement device may be used in system 100. In some embodiments, the external flow measurement device is configured to connect into breathing circuit 106 and includes appropriate means for evaluating when to open and close valve 108.

In some embodiments, system 100 employs its own low-flow port so low-flow port 124 may not even be necessary on ventilator 104. Such a stand-alone device allows this present patent application to be used on any ventilator.

Figure 34:
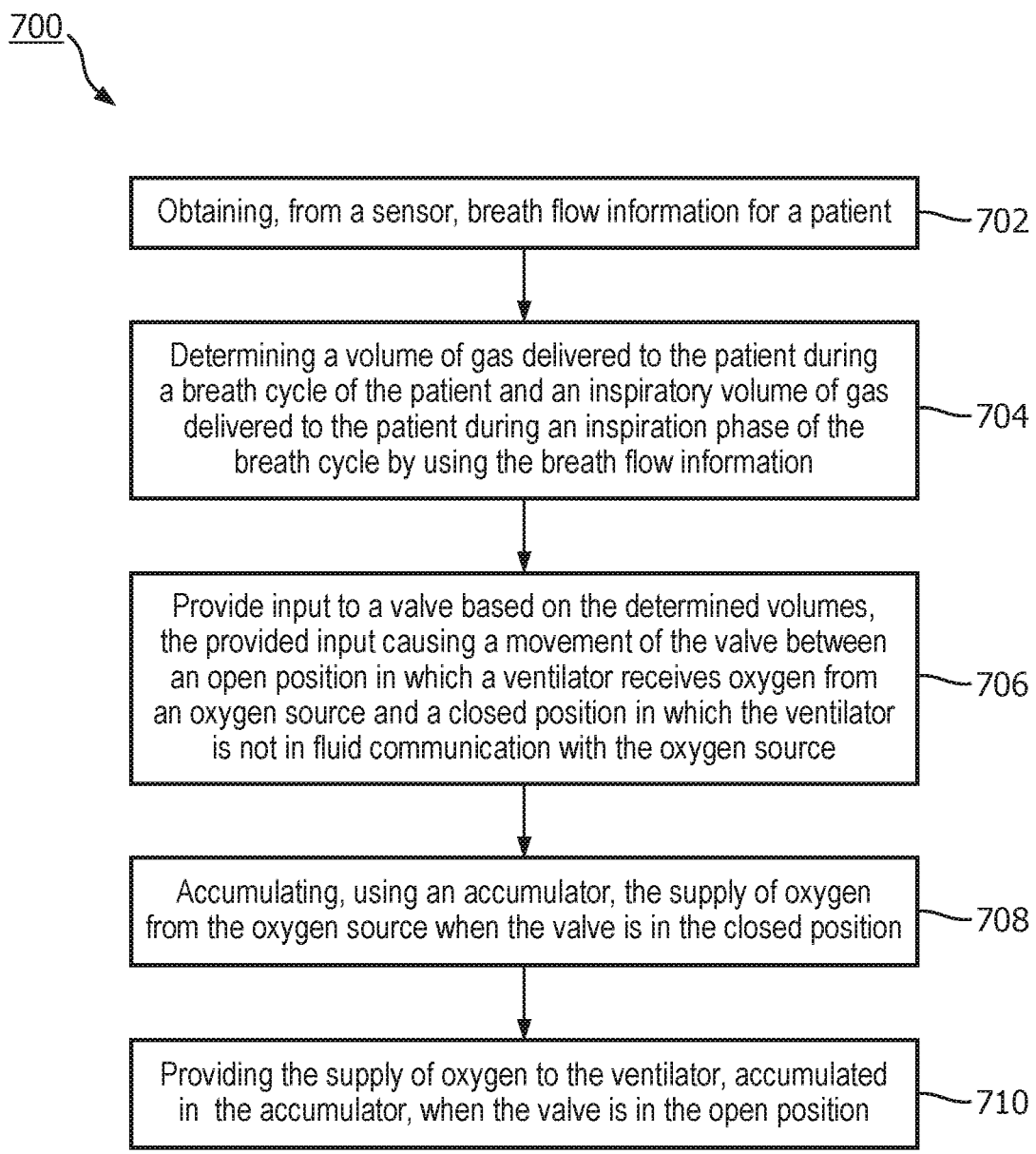
FIG. 34 shows a method for delivering oxygen to a patient in accordance with an embodiment of the present patent application.

Referring to FIG. 34, a method 700 for delivery of oxygen is provided. Method 700 is implemented by computer system 114 that comprises one or more physical processors 116 executing computer program instructions that, when executed, perform method 700. In some embodiments, method 700 comprises: obtaining, from sensor 112, breath flow information for the patient at procedure 702; determining, using computer system 114, a volume of gas delivered to the patient during a breath cycle of the patient and an inspiratory volume of gas delivered to the patient during an inspiration phase of the breath cycle by using the breath flow information at procedure 704; providing, using computer system 114, input to valve 108 based on the determined volumes, the provided input causing a movement of the valve between an open position in which ventilator 104 receives a supply of oxygen from oxygen source 102 and a closed position in which the ventilator is not in fluid communication with the oxygen source at procedure 706; accumulating, using accumulator 110, the supply of oxygen from the oxygen source when the valve is in the closed position at procedure 708; and providing the supply of oxygen to the ventilator, accumulated in the accumulator, when the valve is in the open opening at procedure 710.

Method 700 further comprises: obtaining a tube volume and determining a volume difference between the volume of the gas delivered to the patient during the breath cycle of the patient and the tube volume. Method 700 comprises providing the input to valve 108 causing the movement of valve 108 to the open position when the determined volume difference is delivered to the patient from a start of a next breath cycle. Method 700 comprises maintaining valve 108 in the open position until the inspiratory volume of gas delivered to the patient during the inspiration phase of the breath cycle and providing the input to valve 108 causing the movement of valve 108 to the closed position after the inspiratory volume of gas is delivered to the patient.

In some embodiments, the various computers and subsystems illustrated in FIG. 7 may comprise one or more computing devices that are programmed to perform the functions described herein. The computing devices may include one or more electronic storages (e.g., database 132, or other electronic storages), one or more physical processors programmed with one or more computer program instructions, and/or other components. The computing devices may include communication lines or ports to enable the exchange of information with a network (e.g., network 150) or other computing platforms via wired or wireless techniques (e.g., Ethernet, fiber optics, coaxial cable, WiFi, Bluetooth, near field communication, or other communication technologies). The computing devices may include a plurality of hardware, software, and/or firmware components operating together to provide the functionality attributed herein to the servers. For example, the computing devices may be implemented by a cloud of computing platforms operating together as the computing devices.

The electronic storages may comprise non-transitory storage media that electronically stores information or data. The electronic storage media of the electronic storages may include one or both of system storage that is provided integrally (e.g., substantially non-removable) with the servers or removable storage that is removably connectable to the servers via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information received from the servers, information received from client computing platforms, or other information that enables the servers to function as described herein.

The processors may be programmed to provide information processing capabilities in the system 100. As such, the processors may include one or more of a digital processor, an analog processor, or a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 212-220 (as shown in FIG. 7) or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the subsystems 212-220 (as shown in FIG. 7) described herein is for illustrative purposes, and is not intended to be limiting, as subsystems 212-220 (as shown in FIG. 7) may provide more or less functionality than is described. As another example, additional subsystems may be programmed to perform some or all of the functionality attributed herein to subsystems 212-220 (as shown in FIG. 7).

In some embodiments, system 100 may also include a communication interface that is configured to send the determined valve turn_on and valve turn_off through an appropriate wireless communication method (e.g., Wi-Fi, Bluetooth, internet, etc.) to valve 108 or systems for further processing. In some embodiments, system 100 may include a recursive tuning subsystem that is configured to recursively tune its intelligent decision making subsystem using available data or information to provide better overall valve turn_on and valve turn_off. In some embodiments, intelligent decision making subsystem, communication interface and recursive tuning subsystem may be part of computer system (comprising server 102).

In some embodiments, a subsystem of system 100 is configured to continuously obtain subsequent breath flow information. That is, the subsystem may continuously obtain subsequent breath flow. As an example, the subsequent information may comprise additional information corresponding to a subsequent time (after a time corresponding to information that was used to determine valve turn_on and valve turn_off). The subsequent information may be utilized to further update or modify the valve turn_on and valve turn_off (e.g., new information may be used to dynamically update or modify the valve turn_on and valve turn_off), etc. For example, the subsequent information may also be configured to provide further input to determine the valve turn_on and valve turn_off. In some embodiments, a subsystem of system 100 may be configured to determine the valve turn_on and valve turn_off in accordance with a recursively refined profile (e.g., refined through recursive application of profile refinement algorithms) based on previously collected or subsequent breath flow information.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the present patent application has been described in detail for the purpose of illustration based on what is currently considered to be the most practical and preferred embodiments, it is to be understood that such detail is solely for that purpose and that the present patent application is not limited to the disclosed embodiments, but, on the contrary, is intended to cover modifications and equivalent arrangements that are within the spirit and scope of the appended claims. For example, it is to be understood that the present patent application contemplates that, to the extent possible, one or more features of any embodiment can be combined with one or more features of any other embodiment.

What is claimed is:

1. A system for delivering oxygen, comprising:
an oxygen source;
a ventilator operatively connected to the oxygen source to receive a supply of oxygen therefrom, the ventilator configured to provide gas including a mixture of the supply of oxygen and air to a patient through a breathing circuit;
a valve operatively connected to the ventilator and the oxygen source, the valve having a) an open position in which the ventilator receives the supply of oxygen from the oxygen source and b) a closed position in which the ventilator is not in fluid communication with the oxygen source;
a sensor configured to measure breath flow information for the patient; and
a computer system that comprises one or more physical processors operatively connected with the sensor and the valve, the one or more physical processors being programmed with computer program instructions which, when executed cause the computer system to:
determine a volume of gas delivered to the patient during a breath cycle of the patient and an inspiratory volume of gas delivered to the patient during an inspiration phase of the breath cycle by using the breath flow information;
use the determined volumes to decide when to supply oxygen from the oxygen source; and
thereafter provide input to the valve based on the determined volumes, the provided input causing a movement of the valve between the open and the closed positions.

2. The system of claim 1, wherein the computer system is further configured to: obtain a tube volume; and determine a volume difference between the volume of the gas delivered to the patient during the breath cycle of the patient and the tube volume.

3. The system of claim 2, wherein the computer system is configured to provide the input to the valve causing the movement of the valve to the open position when the determined volume difference is delivered to the patient from a start of a next breath cycle.

4. The system of claim 3, wherein the computer system is configured to maintain the valve in the open position until the inspiratory volume of gas delivered to the patient during the inspiration phase of the breath cycle and to provide input to the valve causing the movement of the valve to the closed position after the inspiratory volume of gas is delivered to the patient.

5. The system of claim 1, wherein the oxygen source is selected from the group consisting of an oxygen concentrator, a portable oxygen concentrator, a pressurized oxygen gas cylinder, a compressed oxygen gas cylinder, an oxygen generator, an oxygen blending module and an oxygen gas bottle.

6. The system of claim 1, wherein the oxygen source is an oxygen concentrator, and further comprising an accumulator configured to accumulate the supply of oxygen from the oxygen source when the valve is in the closed position and to provide the supply of oxygen to the ventilator when the valve is in the open position.

7. A method for delivery oxygen, the method being implemented by a computer system that comprises one or more physical processors executing computer program instructions that, when executed, perform the method, the method comprising:
obtaining, from a sensor, breath flow information for a patient;
determining, using the computer system, a volume of gas delivered to the patient during a breath cycle of the patient and an inspiratory volume of gas delivered to the patient during an inspiration phase of the breath cycle by using the breath flow information;
using the determined volumes to decide when to supply oxygen from an oxygen source; and
thereafter providing, using the computer system, input to a valve based on the determined volumes, the provided input causing a movement of the valve between an open position in which a ventilator receives a supply of oxygen from the oxygen source and a closed position in which the ventilator is not in fluid communication with the oxygen source.

8. The method of claim 7, wherein the method further comprises: obtaining a tube volume; and determining a volume difference between the volume of the gas delivered to the patient during the breath cycle of the patient and the tube volume.

9. The method of claim 8, wherein the method comprises providing the input to the valve causing the movement of the valve to the open position when the determined volume difference is delivered to the patient from a start of a next breath cycle.

10. The method of claim 9, wherein the method comprises maintaining the valve in the open position until the inspiratory volume of gas delivered to the patient during the inspiration phase of the breath cycle and providing the input to the valve causing the movement of the valve to the closed position after the inspiratory volume of gas is delivered to the patient.

11. The method of claim 7, wherein the oxygen source is selected from the group consisting of an oxygen concentrator, a portable oxygen concentrator, a pressurized oxygen gas cylinder, a compressed oxygen gas cylinder, an oxygen generator, an oxygen blending module and an oxygen gas bottle.

12. The method of claim 7, further comprising:
accumulating, using an accumulator, the supply of oxygen from the oxygen source when the valve is in the closed position; and
providing the supply of oxygen to the ventilator, accumulated in the accumulator, when the valve is in the open position.

13. A system for delivering oxygen, the system comprising:
a means for supplying oxygen;
a means for providing gas to a patient through a breathing circuit means, the gas including a mixture of air and a supply of oxygen from the means for supplying oxygen;
an opening and closing means having a) an open position in which the means for providing gas receives the supply of oxygen from the means for supplying oxygen and b) a closed position in which the means for providing gas is not in fluid communication with the means for supplying oxygen; and
a means for executing machine-readable instructions with at least one processor, wherein the machine-readable instructions comprising:
obtaining, from a means for sensing, breath flow information for a patient;
determining, using the means for executing, a volume of gas delivered to the patient during a breath cycle of the patient and an inspiratory volume of gas delivered to the patient during an inspiration phase of the breath cycle by using the breath flow information;
using the means for executing to decide when to supply oxygen from the means for supplying oxygen based on the determined volumes; and
thereafter providing, using the means for executing, input to the opening and closing means based on the determined volumes, the provided input causing a movement of the opening and closing means between the open and closed positions.

14. The system of claim 13, wherein the machine-readable instructions comprising obtaining a tube volume; and determining a volume difference between the volume of the gas delivered to the patient during the breath cycle of the patient and the tube volume.

15. The system of claim 14, wherein the machine-readable instructions comprising providing the input to the opening and closing means causing the movement of the opening and closing means to the open position when the determined volume difference is delivered to the patient from a start of a next breath cycle.

16. The system of claim 15, wherein the machine-readable instructions comprising maintaining the opening and closing means in the open position until the inspiratory volume of gas delivered to the patient during the inspiration phase of the breath cycle and providing the input to the opening and closing means causing the movement of the opening and closing means to the closed position after the inspiratory volume of gas is delivered to the patient.

17. The system of claim 13, wherein the means for supplying oxygen is selected from the group consisting of an oxygen concentrator, a portable oxygen concentrator, a pressurized oxygen gas cylinder, a compressed oxygen gas cylinder, an oxygen generator, an oxygen blending module and an oxygen gas bottle.

18. The system of claim 13, further comprising a means for accumulating the supply of oxygen from the means for supplying oxygen when the opening and closing means is in the closed position and for providing the supply of oxygen to the means for providing gas when the opening and closing means is in the open position.

* * * * *